(12) United States Patent
White et al.

(10) Patent No.: US 7,595,160 B2
(45) Date of Patent: Sep. 29, 2009

(54) ANALYTE DETECTION USING BARCODED POLYMERS

(75) Inventors: Eric Jon White, Londonderry, NH (US); Rudolf Gilmanshin, Framingham, MA (US)

(73) Assignee: U.S. Genomics, Inc., Woburn, MA (US)

( * ) Notice: Subject to any disclaimer, the term of this patent is extended or adjusted under 35 U.S.C. 154(b) by 0 days.

(21) Appl. No.: 11/364,856

(22) Filed: Feb. 27, 2006

(65) Prior Publication Data

US 2009/0215032 A1    Aug. 27, 2009

Related U.S. Application Data

(63) Continuation-in-part of application No. 11/035,417, filed on Jan. 13, 2005.

(60) Provisional application No. 60/656,869, filed on Feb. 25, 2005, provisional application No. 60/536,157, filed on Jan. 13, 2004.

(51) Int. Cl.
C12Q 1/68 (2006.01)
C12P 19/34 (2006.01)
C12N 15/11 (2006.01)
C07H 21/04 (2006.01)

(52) U.S. Cl. .......................... 435/6; 435/91.1; 536/23.1

(58) Field of Classification Search .................. None
See application file for complete search history.

(56) References Cited

U.S. PATENT DOCUMENTS

| | | | |
|---|---|---|---|
| 5,190,756 A * | 3/1993 | Castellino et al. | 424/94.64 |
| 6,287,772 B1 * | 9/2001 | Stefano et al. | 435/6 |
| 6,331,414 B1 * | 12/2001 | Lee et al. | 435/69.4 |
| 6,511,809 B2 | 1/2003 | Baez et al. | |
| 6,927,065 B2 | 8/2005 | Chan et al. | |
| 7,262,859 B2 | 8/2007 | Larson et al. | |
| 7,282,330 B2 | 10/2007 | Zhao et al. | |
| 7,351,538 B2 | 4/2008 | Fuchs et al. | |
| 7,371,520 B2 | 5/2008 | Zhao et al. | |
| 7,402,422 B2 | 7/2008 | Fuchs et al. | |
| 2002/0051986 A1 | 5/2002 | Baez et al. | |
| 2002/0192687 A1 * | 12/2002 | Mirkin et al. | 435/6 |
| 2007/0166743 A1 | 7/2007 | Gilmanshin | |
| 2008/0003689 A1 | 1/2008 | Lee et al. | |
| 2008/0085552 A1 | 4/2008 | Larson et al. | |
| 2008/0103296 A1 | 5/2008 | Zhao et al. | |
| 2008/0254549 A1 | 10/2008 | Fuchs et al. | |

FOREIGN PATENT DOCUMENTS

| | | |
|---|---|---|
| WO | WO 96/29593 A1 | 9/1996 |
| WO | WO 96/30508 A1 | 10/1996 |
| WO | WO 97/00446 A1 | 1/1997 |
| WO | WO 98/10097 A2 | 3/1998 |
| WO | WO 98/35012 A2 | 8/1998 |
| WO | WO 99/05315 A2 | 2/1999 |
| WO | WO 00/09757 A1 | 2/2000 |
| WO | WO 00/60072 A1 | 10/2000 |
| WO | WO 00/60114 A2 | 10/2000 |
| WO | WO 01/13088 A1 | 2/2001 |
| WO | WO 01/61037 A1 | 8/2001 |
| WO | WO 02/099398 A1 | 12/2002 |
| WO | WO 02/101095 A1 | 12/2002 |
| WO | WO 02/101353 A2 | 12/2002 |
| WO | WO 03/025540 A2 | 3/2003 |
| WO | WO 03/091455 A1 | 11/2003 |
| WO | WO 03/100101 A1 | 12/2003 |
| WO | WO 2004/007692 A2 | 1/2004 |
| WO | WO 2004/048514 A2 | 6/2004 |
| WO | WO 2004/066185 A1 | 8/2004 |
| WO | WO 2004/091795 A2 | 10/2004 |
| WO | WO 2005/012575 A1 | 2/2005 |
| WO | WO 2005/017205 A2 | 2/2005 |
| WO | WO 2005/022162 A1 | 3/2005 |
| WO | WO 2008/024483 A1 | 2/2008 |
| WO | WO 2008/085991 A2 | 7/2008 |
| WO | WO 2008/111959 A2 | 9/2008 |
| WO | WO 2009/009127 A2 | 1/2009 |

OTHER PUBLICATIONS

Lewin, Gene Expression, vol. 2, 1974, John Wiley & Sons, New York, pp. 148-153.*

Landegren et al., Padlock and proximity probes for in situ and array-based analyses: tools for the post-genomic era. Comparative and Functional Genomics. 2003;4:525-530.

Taussig et al., Progress in antibody arrays. Drug Discovery Today: Targets. 2003;2(4):169-176.

Ambrose et al., Application of single molecule detection to DNA sequencing and sizing, Ber. Bunsenges. Phys. Chem. 1993; 97:1535-1542.

Aston et al., Optical mapping and its potential for large-scale sequencing projects. Trends Biotechnol. Jul. 1999;17(7):297-302.

Bensimon et al., Alignment and sensitive detection of DNA by a moving interface. Science. Sep. 30, 1994;265(5181):2096-8. Abstract Only.

Caplin et al., LightCycler hybridization probes: the most direct way to monitor PCR amplification for quantification and mutation detection. Biochemica. 1999;1:5-8.

Castro et al., Single-Molecule Electrophoresis: Applications to Biomolecular Detection. SPIE. 1995; 2396:79-85.

Chan et al., DNA mapping using microfluidic stretching and single-molecule detection of fluorescent site-specific tags. Genome Res. Jun. 2004;14(6):1137-46.

Dittrich et al., Sorting of cells and single particles in microstructures. Biophys J. Feb. 24, 2002;82(1):43a.

Eigen et al., Sorting single molecules: Application to diagnostics and evolutionary biotechnology. Proc Natl Acad Sci U S A. Jun. 21, 1994;91(13):5740-7.

(Continued)

Primary Examiner—James Martinell
(74) Attorney, Agent, or Firm—Wolf, Greenfield & Sacks, P.C.

(57) ABSTRACT

The invention relates to methods and systems for identifying, quantitating and/or analyzing analytes from samples. The analytes may be organic or inorganic in nature and include but are not limited to pathogens such as viruses.

20 Claims, 9 Drawing Sheets

OTHER PUBLICATIONS

Ekstrøm et al., Two-point fluorescence detection and automated fraction collection applied to constant denaturant capillary electrophoresis. Biotechniques. Sep. 2000;29(3):582-4, 586-9.

Gaines et al., A new method for measuring lymphoproliferation at the single-cell level in whole blood cultures by flow cytometry. J Immunol Methods. Sep. 9, 1996;195(1-2):63-72.

Herrick et al., H Imaging of single DNA molecule: applications to high-resolution genomic studies. Chromosome Res. 1999; 7(6):409-423.

Jing et al., Automated high resolution optical mapping using arrayed, fluid-fixed DNA molecules. Proc Natl Acad Sci U S A. Jul. 7, 1998;95(14):8046-51.

Kasianowicz et al., Polymer transport in the alpha-hemolysin ion channel. p. 111. Abstract 26.

Kasianowicz et al., Characterization of individual polynucleotide molecules using a membrane channel. Proc Natl Acad Sci U S A. Nov. 26, 1996;93(24):13770-3.

Kinjo et al., Ultrasensitive hybridization analysis using fluorescence correlation spectroscopy. Nucleic Acids Res. May 25, 1995;23(10):1795-9.

Korn et al., Gene expression analysis using single molecule detection. Nucleic Acids Res. Aug. 15, 2003;31(16):e89. 8 pages.

Lee et al., Laser-induced fluorescence detection of a single molecule in a capillary. Anal Chem. Dec. 1, 1994;66(23):4142-9.

McBride et al., Multiplexed liquid arrays for simultaneous detection of simulants of biological warfare agents. Anal Chem. Apr. 15, 2003;75(8):1924-30. Abstract Only.

Meng et al., Optical mapping of lambda bacteriophage clones using restriction endonucleases. Nat Genet. Apr. 1995;9(4):432-8.

Mertz et al., Single-molecule detection by two-photon-excited fluorescence. Optics Letts. Dec. 15, 1995;20(24):2532-4.

Nie et al., Probing individual molecules with confocal fluorescence microscopy. Science. Nov. 11, 1994;266(5187):1018-21.

Otobe et al., Behavior of DNA fibers stretched by precise meniscus motion control. Nucleic Acids Res. Nov. 15, 2001;29(22):E109, 6 pages.

Parra et al. High resolution visual mapping of stretched DNA by fluorescent hybridization. Nat Genet. Sep. 1993;5(1):17-21. Abstract Only.

Peck et al., Single-molecule fluorescence detection: autocorrelation criterion and experimental realization with phycoerythrin. Proc Natl Acad Sci U S A. Jun. 1989;86(11):4087-91.

Saffran et al., Site-directed psoralen crosslinking of DNA. Proc Natl Acad Sci U S A. Aug. 1982;79(15):4594-8.

Schwartz et al., Separation of yeast chromosome-sized DNAs by pulsed field gradient gel electrophoresis. Cell. May 1984;37(1):67-75. Abstract Only.

Schwartz et al., Ordered restriction maps of *Saccharomyces cerevisiae* chromosomes constructed by optical mapping. Science. Oct. 1, 1993;262(5130):110-4. Abstract Only.

Shera et al., Detection of single fluorescent molecules. Chem Phys Letts. 1990; 174(6): 553-7.

Shortreed et al., High-throughput single-molecule DNA screening based on electrophoresis. Anal Chem. Jul. 1, 2000;72(13):2879-85.

Van Oss et al., Kinetics and energetics of specific intermolecular interactions. J Mol Recognit. Sep.-Oct. 1997;10(5):203-16. Abstract Only.

Wang et al., Fluorescence resonance energy transfer between donor-acceptor pair on two oligonucleotides hybridized adjacently to DNA template. Biopolymers. 2003;72(6):401-12.

Xu et al., Multiplexed SNP genotyping using the Qbead system: A quantum dot-encoded microsphere-based assay. Nucleic Acids Res. Apr. 15, 2003;31(8):E43-1-E43-10.

\* cited by examiner

Different sequence composition of between nicking sites creates unique ligation junctions 1-4 to ensure correct digital DNA assembly Block 1
Block 0

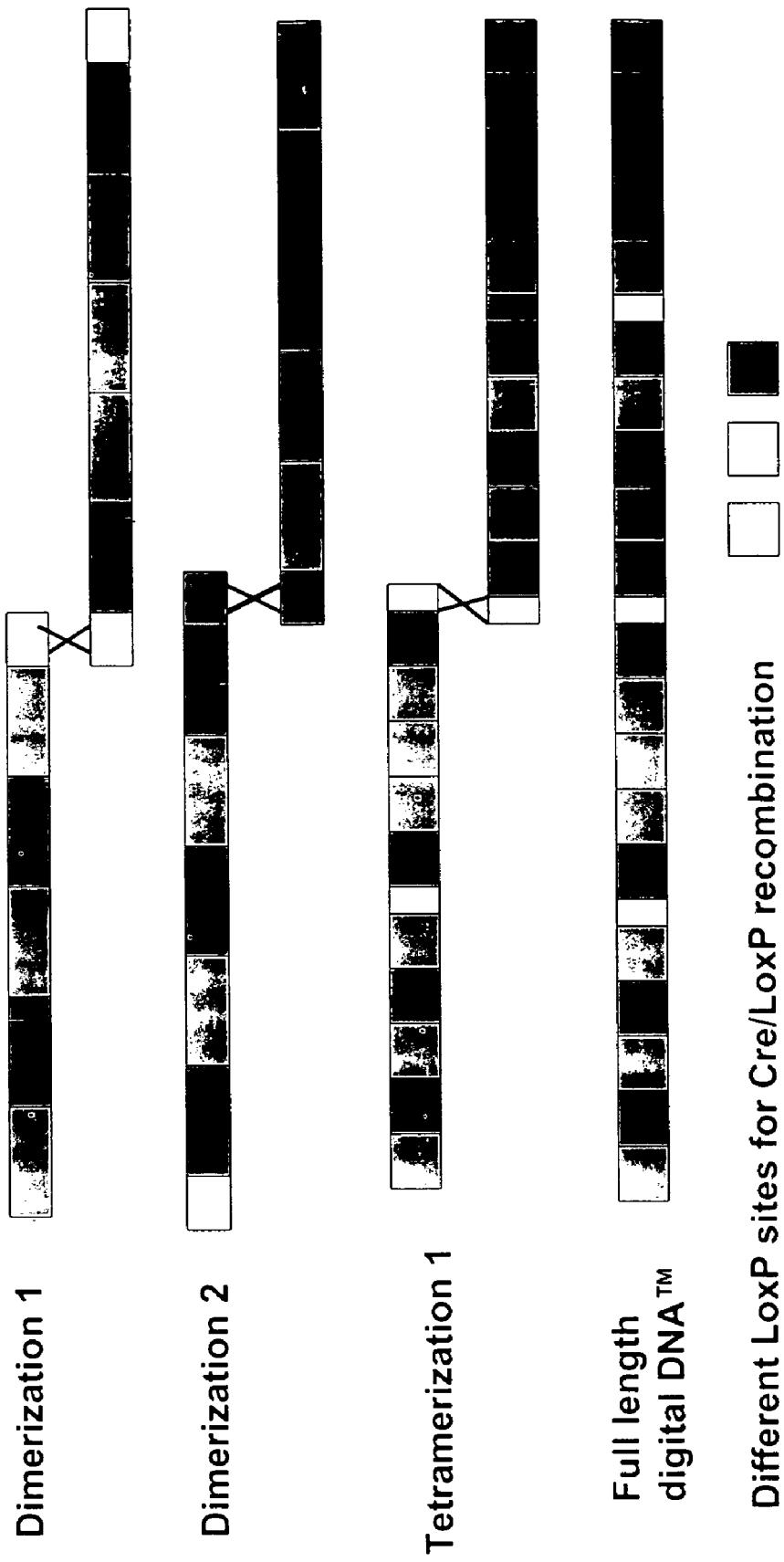

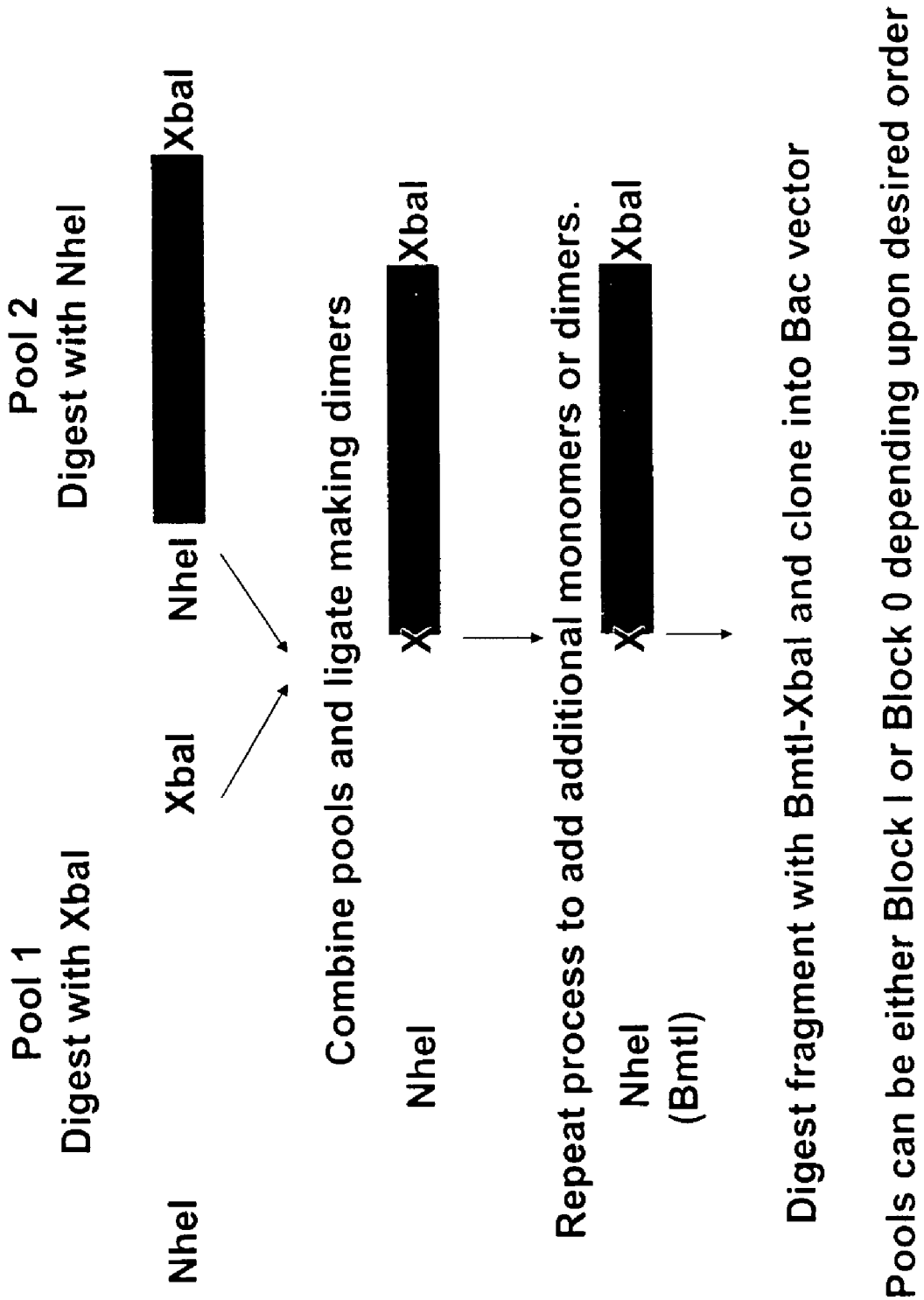

ANALYTE DETECTION USING BARCODED POLYMERS

RELATED APPLICATION

This application is a continuation-in-part of U.S. application Ser. No. 11/035,417, filed Jan. 13, 2005, which claims priority to U.S. Provisional Application Ser. No. 60/536,157, filed Jan. 13, 2004, and also claims priority to U.S. Provisional Application Ser. No. 60/656,869, entitled "ANALYSIS OF POLYMERS", filed Feb. 25, 2005, the entire contents of each of which are incorporated by reference herein.

FIELD OF THE INVENTION

The invention relates, inter alia, to detection and quantitation of analytes.

BACKGROUND OF THE INVENTION

Multiplexing refers to the ability to analyze (e.g., detect) more than one, and preferably many, different substances simultaneously. The ability to perform a multiplexed analysis would be advantageous to a number of applications such as proteomics, clinical analysis of body fluids, biodefence, and the like. Applications involving a limited amount of sample or a low concentration of the substances to be detected (i.e., analytes) particularly benefit from multiplexing capability. Preferably, multiplexing systems should demonstrate a high sensitivity, a wide dynamic range, and significant multiplexing capability.

SUMMARY OF THE INVENTION

The invention relates generally to detection of analytes using polymer based methods and compositions. The invention is capable of detecting, quantifying and also harvesting and further analyzing analytes in a sample. The methods and compositions relate to the use of polymers as analyte capture agents and as analyte identifiers. A high degree of multiplexing is possible given the diversity in available polymers and analyte-specific binding partners.

Thus, in one aspect, the invention provides an isolated nucleic acid comprising a non-specific spacer sequence, an analyte capture sequence that comprises binding sites for analyte adaptor compounds, and optionally an identifier sequence that also optionally comprises binding sites for identifier compounds, wherein the non-specific spacer sequence and the analyte capture sequence lack binding sites for identifier compounds.

In one embodiment, the identifier compounds are identifier oligonucleotides. In another embodiment, the identifier compounds are nucleic acid binding proteins such as but not limited to transcription factors and restriction enzymes.

In one embodiment, the analyte adaptor compounds are analyte adaptor oligonucleotides. In another embodiment, the analyte adaptor compounds are proteins.

In one embodiment, the non-specific spacer sequence has a length that exceeds a detection system resolution limit. In another embodiment, the non-specific spacer sequence and the analyte capture sequence have a sum total length that exceeds a detection system resolution limit.

In one embodiment, the identifier sequence is located within the non-specific spacer sequence. In one embodiment, the non-specific spacer sequence is divided into more than one, including two, three or more, sequences. In one embodiment, the non-specific spacer sequence is *Autographa californica* nucleic acid sequence.

In one embodiment, the identifier sequence comprises binding sites for identifier compounds. In another embodiment, the identifier sequence does not comprise binding sites for identifier compounds.

In one embodiment, the composition further comprises an identifier compound such as an identifier oligonucleotide bound to the nucleic acid, either covalently or non-covalently. In one embodiment, the identifier oligonucleotide is a bis-peptide nucleic acid that is detectably labeled with but not limited to a fluorophore. In another embodiment, the identifier oligonucleotide is a triplex forming oligonucleotide that is detectably labeled with but not limited to a fluorophore.

In one embodiment, the composition further comprises an analyte adaptor compound such as an analyte adaptor oligonucleotide bound to the nucleic acid, either covalently or non-covalently. In one embodiment, the analyte adaptor oligonucleotide is a bis-peptide nucleic acid. In another embodiment, the analyte adaptor oligonucleotide is a triplex forming oligonucleotide.

In one embodiment, the analyte adaptor compound is an analyte-specific binding partner (e.g., a primary analyte-specific binding partner). In this embodiment, the analyte adaptor compound binds analytes directly. In a related embodiment, the analyte adaptor oligonucleotide comprises an aptamer that bind analyte directly.

In another embodiment, the analyte adaptor compound is bound to an analyte-specific binding partner, either covalently or non-covalently. In a related embodiment, the analyte adaptor compound is an analyte adaptor oligonucleotide that is bound to an analyte-specific binding partner that is a peptide (e.g., an antibody or an antibody fragment).

In one embodiment, the composition further comprises an analyte bound to the nucleic acid via the analyte adaptor compound, and optionally the analyte-specific binding partner. The composition may further comprise a secondary analyte-specific binding partner bound to the analyte. The secondary analyte-specific binding partner may further comprise a detectable label.

In one embodiment, the isolated nucleic acid comprises a 5' and/or a 3' overhang. In a related embodiment, the overhangs are not complementary to each other.

In one embodiment, the nucleic acid is about 9 kb, 10 kb or 111 kb in length.

In another aspect, the invention provides an isolated composite nucleic acid comprising a plurality of the afore-mentioned isolated nucleic acids linked to each other in a non-random manner, wherein each member of the plurality (a) either comprises or does not comprise binding sites for identifier compounds, and (b) has an identical analyte-binding specificity, and wherein the plurality are linked to each other in a non-random manner to form an identifier sequence pattern. The identifier sequence pattern is the order of identifier sequences, wherein such sequences are distinguished based on whether they comprise or do not comprise binding sites for identifier compounds.

Many of the afore-mentioned embodiments apply equally to the composite nucleic acid aspects of the invention.

Depending on the embodiment, the plurality is 2, 3, 4, 5, 6, 7, 8, 9, 10, 11, 12, 13, 14, 15, 16, 17, 18, 19, 20 or more nucleic acids.

In one embodiment, each member of the plurality has a length of about 9 kb, about 10 kb, or about 11 kb. In another embodiment, the composite nucleic acid has a length of about 10 kb to about 200 kb.

In one embodiment, the composite nucleic acid is bound to identifier compounds such as identifier oligonucleotides and analyte adaptor compounds such as analyte adaptor oligonucleotides.

In other aspects, the invention provides vectors and cells comprising the afore-mentioned nucleic acids of the invention.

In still another aspect, the invention provides a method of synthesizing a composite nucleic acid comprising assembling a plurality of the afore-mentioned isolated nucleic acids in a non-random manner, to form a composite nucleic acid, wherein each member of the plurality (a) either comprises or does not comprise binding sites for identifier compounds, (b) has an identical analyte-binding specificity, and (c) has 5' and 3' overhangs, wherein the 5' overhang of one member is specific and complementary to the 3' overhang of another member, except that a single 5' overhang and a single 3' overhang within the plurality do not have respective complementary 3' and 5' overhangs within the plurality.

In one embodiment, the plurality of isolated nucleic acids are assembled by directional cloning. In one embodiment, the plurality of isolated nucleic acids are assembled by homologous recombination. In another embodiment, the plurality of isolated nucleic acids are assembled by direction cloning and homologous recombination.

In one embodiment, the 5' and 3' overhangs are generated using nicking enzymes.

In still another aspect, the invention provides a method of detecting an analyte comprising contacting a sample to an afore-mentioned composite nucleic acid for a time and under conditions sufficient to allow an analyte, if present in the sample, to bind to the composite nucleic acid, contacting the sample to a secondary analyte-binding partner that comprises a label that is detectable and distinct from detectably labeled identifier compounds, and determining (a) a pattern of detectably labeled identifier compounds bound to the composite nucleic acid and (b) an amount of secondary analyte-binding partner bound to the composite nucleic acid. The pattern of detectably labeled identifier compounds bound to the nucleic acid indicates the identity of the analyte, and the amount of secondary analyte-binding partner bound to the composite nucleic acid that exceeds a control indicates the presence of analyte in the sample.

In one embodiment, the sample is an air, water or swab sample. In another embodiment, the sample is a biological fluid or tissue.

In one embodiment, the analyte is a biowarfare agent, or a component thereof. In one embodiment, the analyte is a nucleic acid.

In one embodiment, the secondary analyte-binding partner is an antibody or antigen-binding antibody fragment.

In one embodiment, the label is a fluorophore.

These and other embodiments of the invention will be described in greater detail herein.

Each of the limitations of the invention can encompass various embodiments of the invention. It is therefore anticipated that each of the limitations of the invention involving any one element or combinations of elements can be included in each aspect of the invention. This invention is not limited in its application to the details of construction and/or the arrangement of components set forth in the following description or illustrated in the drawings. The invention is capable of other embodiments and of being practiced or of being carried out in various ways.

The phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

BRIEF DESCRIPTION OF THE DRAWINGS

FIG. 8 illustrates another construction strategy for composite nucleic acids (i.e., "Digital DNA™"). This strategy involves dimerization and tetramerization of nucleic acid segments to form a composite nucleic acid using Cre/LoxP homologous recombination.

FIG. 9 illustrates another construction strategy for composition nucleic acids (i.e., "Digital DNA™"). This strategy involves multimerization by restriction enzyme digest. Pools such as pool 1 or pool 2 can be either "1" or "0" segment pools, depending upon desired order.

BRIEF DESCRIPTION OF THE SEQUENCE LISTING

Figure 1:
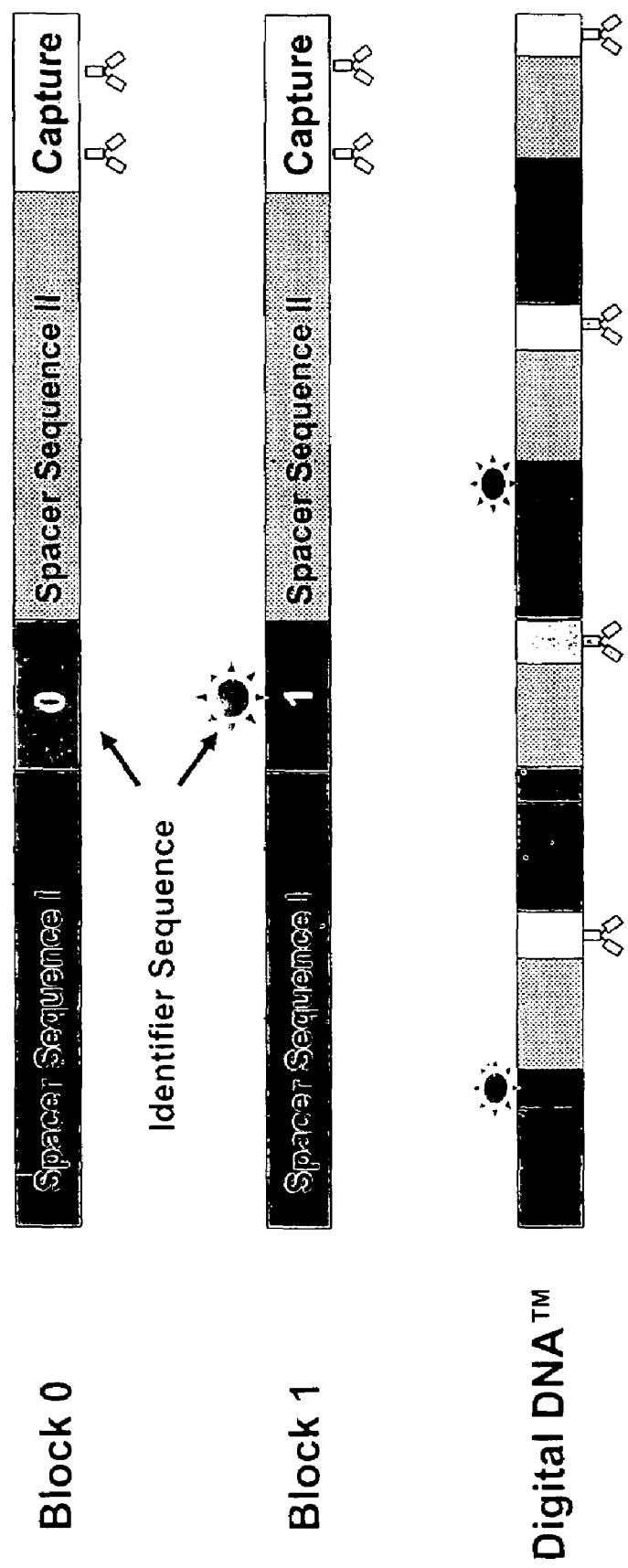
FIG. 1 illustrates two generic nucleic acid segments (denoted "0" and "1"), and a composite nucleic acid (denoted a "Digital DNA™").

SEQ ID NO: 1 is the nucleotide sequence of a binding site for a triplex forming oligonucleotide.

SEQ ID NO: 2 is the nucleotide sequence of a binding site for a triplex forming oligonucleotide.

SEQ ID NO: 3 is the nucleotide sequence of a segment end that can be digested with a nicking enzyme.

SEQ ID NO: 4 is the nucleotide sequence of a segment end that can be digested with a nicking enzyme.

SEQ ID NO: 5 is the nucleotide sequence of a segment end that can be digested with a nicking enzyme.

DETAILED DESCRIPTION OF THE INVENTION

The invention in its broadest sense relates to detecting one or more analytes. The invention employs polymer-based methods to detect and identify, and optionally quantify, analytes. The method is particularly suited to determining analyte presence or concentration in a sample wherein the sample is rare or the analyte concentration is low.

The invention employs polymer-based products for detecting analytes. In preferred embodiments, the polymers are nucleic acids. The nucleic acid has dual functionality. First, it binds analyte, directly or indirectly. Second, it is a surrogate marker for the analyte being detected. Each nucleic acid has a particular analyte binding specificity and a particular label (or labeling pattern) that indicates the analyte binding specificity. The label (or labeling pattern) is analogous to a barcode. The label (or labeling pattern) is read, analogous to reading a barcode, in order to determine the analyte binding specificity of the polymer. Analyte presence is determined based on the presence of an analyte specific signal (such as a detectable label conjugated to a secondary analyte-specific binding partner).

The invention also provides the building blocks of these nucleic acids. In the broadest aspect, these building blocks are divided into two categories: those that emit an "identifier" signal and those that do not. The presence of the identifier signal may be read and recorded by a detection system as for example "1", while absence of the signal may be read and recorded as for example "0". The building blocks are then linked together to form a larger nucleic acid having a non-random arrangement of 1's and 0's. In this way, the larger nucleic acid can have a unique sequence of 1's and 0's, akin to a digital barcode. As an example, nucleic acids composed of two building blocks can be arranged as "10", "01", "00" or "11". The four different combinations can be used as identifiers for four different analytes. If nucleic acids composed of three building blocks are used, eight or $2^3$ combinations are possible. This results in identifiers for eight different analytes. As will be understood, the longer the nucleic acid (i.e., the more building blocks it contains), the more identifier sequences and the more analytes that can be detected, provided other factors are non-limiting.

The detection of more than one analyte in a single analysis (or run) of a sample is referred to herein as multiplexing. The degree of multiplexing in any given analysis will depend on the particular application and the number of analytes to be detected. The degree of multiplexing may also be limited by the throughput rate of the specific detection system used. The invention contemplates that the degree of multiplexing may be 2 (i.e., 2 analytes can be detected in a single analysis), 3, 4, 5, 6, 7, 8, 9, 10, at least 20, at least 50, at least 100, at least 500, at least 1000, at least 5000, at least 10000, at least 100000, or higher.

The invention provides composite nucleic acids and the nucleic acid segments (i.e., the building blocks referred to herein) used to make them. A composite nucleic acid as used herein is a nucleic acid made up of at least two and preferably more segments, conjugated to each other in a non-random manner. The composite may be made up of 2, 3, 4, 5, 6, 7, 8, 9, 10, 11, 12, 13, 14, 15, 16, 17, 18, 19, 20, or more segments. As described in greater detail herein, the non-random arrangement of segments results in the barcode that identifies the analyte.

Each segment itself comprises a number of regions or elements, each of which has a particular function as described herein. Generally, each segment comprises a non-specific spacer sequence, an identifier sequence, and an analyte capture sequence. As will be understood in the context of this description, identifier sequences that are designed to not emit signal may simply be additional non-specific spacer sequence. Therefore, some segments may comprise spacer sequence and analyte capture sequence.

The location of these sequences relative to each other and along the length of the segment can vary, although it is preferable that their location be relatively uniform across the plurality of segments that make a composite nucleic acid and also in some embodiments across the segments that make up different composite nucleic acids. The identifier sequence and the analyte capture sequence can be located adjacent each other, provided their signals do not interfere with each other. The segments that make up a single composite nucleic acid have the same analyte binding specificity.

The length of segments that make up a composite should be relatively uniform, both within a composite and within a pool of different composites. The exact length will vary, depending upon the resolution limit of the detection system ultimately used to analyze the nucleic acid. The resolution limit is the distance that two signals must be located away from each other in order for a detection system to distinguish them and record them as separate signals (or events). For example, if the detection system has a resolution limit of 10 kb, then signals that are located less than 10 kb away from each other will not be distinguished, and the system will record one rather than two events. Reference can be made to published U.S. Patent Application Publication No. 20030059822A1 and/or published PCT Application No. WO 03/025540 for a discussion of resolution limits. Therefore, the distance between identifier sequences, and optionally between analyte capture sequences, should approximate or exceed the resolution limit of the detection system.

The length of the segment therefore will depend on these distances and the lengths of the identifier and analyte capture sequences themselves. The segment may therefore have any suitable length, including but not limited to between 1-5 kb, 5-10 kb, 7.5-10 kb, 7.5-12.5 kb, 7.5-15 kb, and any integer therebetween as if explicitly recited herein. In some embodiments, the segment has a length of about 9 kb, about 10 kb, or about 11 kb.

The length of the identifier and analyte capture sequences will depend on the number of binding sites each has and the length of those sites. In some instances, it is preferred that the identifier and analyte capture sequences are as short as possible, without compromising signal detection from either sequence. In some embodiments, each identifier and analyte capture sequence represents equal to or less than 25%, 20%, 15%, 10%, 5% or less of the segment length. The identifier sequence length should be relatively uniform across the composite. Similarly, analyte capture sequence length should be relatively uniform across the composite. The length of the identifier sequence however may differ from the length of the analyte capture sequence. In some embodiments, the identifier sequence will have a length of at least 0.1, 0.2, 0.3, 0.4, 0.5, 0.6, 0.7, 0.8, 0.9, or 1 kb. In some embodiments, the analyte capture sequence will have a length of at least 0.1, 0.2, 0.3, 0.4, 0.5, 0.6, 0.7, 0.8, 0.9, 1, 1.5, 2, 2.5, 3 or 3.5 kb.

The length of the composite will vary depending on the number of segments it contains and the length of those segments. In some instances, the length may range from 5-250 kb, although it may be longer, depending on the degree of multiplexing desired. It is to be understood that the longer the composite, the greater the degree of multiplexing.

For the sake of brevity and convenience, analyte detection and quantitation methods and products are primarily described herein with respect to composite nucleic acids. However, the invention applies equally to analyte detection and quantitation using nucleic acid segments individually also.

An identifier sequence as used herein refers to sequence that imparts information about the analyte capture (or binding) specificity of the nucleic acid. This is generally accomplished via the linear arrangement and order of identifier sequences (and thus segments) in a composite nucleic acid. The identifier sequences either will or will not emit a signal. Signal emission is generally accomplished by binding a detectable compound to the identifier sequence. As used herein, these compounds are referred to as identifier compounds. These compounds bind in a sequence-dependent manner, although the sequence requirement may vary between compounds. As described in greater detail herein, binding of these compounds may occur covalently or non-covalently.

Examples of compounds that bind to the identifier sequence in a sequence-dependent manner include other nucleic acids such as oligonucleotides that comprise DNA, RNA, locked nucleic acid (LNA), or peptide nucleic acid (PNA) elements, or mixtures thereof. Particular examples include bis-PNA (described in greater detail herein), and triplex forming oligonucleotides that bind to the nucleic acid by wrapping around the duplex. In some important embodiments, the identifier compounds are oligonucleotides and these are referred to herein as identifier oligonucleotides.

In some instances, the oligonucleotide will form at least a Watson-Crick bond with the identifier sequence. In other instances, the oligonucleotide can form a Hoogsteen bond with the identifier sequence, thereby forming a triplex. An oligonucleotide that binds by Hoogsteen binding enters the major groove of a nucleic acid and hybridizes with the bases located there. Examples include molecules that recognize and bind to the minor and major grooves of nucleic acids (e.g., some forms of antibiotics). Some oligonucleotides such as triplex forming oligonucleotides bind in the major groove of DNA without significant distortion of the DNA helix. This is useful since the ability of the nucleic acid to be stretched (e.g., during interrogation) is not impacted. In some embodiments, the oligonucleotides can form both Watson-Crick and Hoogsteen bonds with the nucleic acid polymer. BisPNA probes, for instance, are capable of both Watson-Crick and Hoogsteen binding to a nucleic acid.

The oligonucleotides can be any length including but not limited to 8-100 nucleotides, 8-75 nucleotides, 8-50 nucleotides, 8-30 nucleotides, 18-30 nucleotides, and every integer therebetween as if explicitly recited herein.

The oligonucleotides are preferably single stranded, but they are not so limited. For example, when the oligonucleotide is a bisPNA it can adopt a secondary structure with the identifier sequence resulting in a triple helix conformation, with one region of the bisPNA forming Hoogsteen bonds with the backbone of the identifier sequence and another region of the bisPNA forming Watson-Crick bonds with the bases of the identifier sequence.

The binding of the oligonucleotide to the composite nucleic acid via hybridization can be manipulated based on the hybridization conditions. For example, salt concentration and temperature can be modulated in order to vary the range of sequences recognized by the oligonucleotides. Those of ordinary skill in the art will be able to determine optimum conditions for a desired specificity. In some embodiments, the hybridization conditions are stringent so that only completely complementary oligonucleotides will bind to the identifier sequence. In other embodiments, less than stringent conditions are used.

Sequence-dependent binding when used in the context of a compound that binds to a nucleic acid means that the compound recognizes a particular linear arrangement of nucleotides in the nucleic acid. In the case of oligonucleotides, the linear arrangement includes contiguous nucleotides that each binds to a corresponding complementary nucleotide in the oligonucleotide.

Other compounds that bind to the identifier sequence in a sequence-dependent manner include nucleic acid binding proteins such as transcription factors that bind promoter or enhancer sequences, polymerases such as DNA or RNA polymerase, restriction enzyme that recognize and bind to their recognition sequence but do not cleave based on particular conditions, methylases, mismatch repair enzymes, chromatin modifying complexes, proteins involved in RNA interference, and the like. The binding (and if necessary recognition) sequences of these proteins are known in the art.

Restriction enzymes may be contacted with identifier sequences under conditions and for times that allow the enzymes to bind to the nucleic acids in a sequence-dependent manner but without cleaving the nucleic acid. For example, reducing the concentration of certain divalent cations (e.g., Mg+2), as described in published US patent application US20050123944A1 published on Jun. 9, 2005, allows a restriction enzyme to bind but not cleave its target nucleic acid.

Other compounds have a more lax sequence requirement. For example, some compounds such as Hoechst 33258 bind to AT-rich regions. An AT-rich sequence can have any length within the parameters set forth herein including at least 0.1, 0.2, 0.3, 0.4, 0.5, 0.6, 0.7, 0.8, 0.9, or 1 kb. The identifier sequence may therefore be partially or completely AT-rich. The degree of AT-richness will vary depending at least on the length of the sequence. Longer sequences may tolerate lower AT content. Generally, the sequence should be at least 60% AT, although preferably the AT content should be higher (e.g., at least 65%, 70%, 75%, 80%, 85%, 90%, 95% or 100%).

Still other compounds such as chromomycin A3 (CMA) or mithramycin A (MMA) bind to GC-rich regions. A GC-rich sequence can have any length within the parameters set forth herein including at least 0.1, 0.2, 0.3, 0.4, 0.5, 0.6, 0.7, 0.8, 0.9, or 1 kb. The identifier sequence may therefore be partially or completely GC-rich. The degree of GC-richness will vary depending at least on the length of the sequence. Longer sequences may tolerate lower GC content. Generally, the sequence should be at least 60% GC, although preferably the GC content should be higher (e.g., at least 65%, 70%, 75%, 80%, 85%, 90%, 95% or 100%).

It is to be understood that when AT- or GC-rich sequences are used as the identifier sequences, then the remainder of the segment must lack either type of sequence so as to prevent false positive identifier signals. For example, if the identifier sequence is AT-rich, then the remaining segment sequence is not AT-rich. If the identifier sequence is GC-rich, then the remaining segment sequence is not GC-rich.

Other sequence-dependent binding compounds include pyrrole-imidazole polyamides as described in published US patent application US20060014163A1 published on Jan. 19, 2006.

Covalent binding of identifier compounds including identifier oligonucleotides to composite nucleic acids can be achieved in a number of ways including but not limited the use of identifier compounds that comprise crosslinkers. Such crosslinkers will covalently bind to composite nucleic acids, following sequence-dependent recognition and non-covalent binding of the identifier compound to the composite. Examples of crosslinkers include furocoumarins (e.g., haloalkyl furocoumarins and haloalkyl coumarin), benzodipyrones (e.g., haloalkyl benzodipyrone), bis-azides (e.g., bis-azido ethidium bromide and azido nucleoside triphosphate), and psoralens (e.g., 8-methoxypsoralen, 5-methoxypsoralen, 4,5',8-trimethylpsoralen, 4'-hydroxymethyl-4,5',8-trimethylpsoralen and 4'-aminomethyl-4,5',8-trimethylpsoralen). Other crosslinkers are provided in U.S. Pat. No. 4,599,303, issued on Jul. 8, 1996.

In some instances, the identifier compound is an oligonucleotide that is conjugated to a peptide-based compound. Covalent conjugation of end-labeled nucleic acids to peptides can be accomplished by SPDP-SATA crosslinking.

The identifier sequence will comprise one and preferably more binding (or recognition) sites for the afore-mentioned compounds. The number and nature of these binding sites will depend upon the compound being used and its sequence requirements. The Examples provide examples of such binding sites for triplex forming oligonucleotides. If the identifier sequence is an AT-rich or a GC-rich sequence, its entire length may be regarded as a binding site.

It is to be understood that for an analysis of a given sample using a plurality of different composite nucleic acids, it is preferable that all identifier sequences within the plurality be identical with regards to their position within a segment, and, if they are signal emitting identifier sequences, the number and nature of binding sites they contain. This will facilitate the detection of identifier sequences (and thus analyte identification) by requiring the use of only one type of compound that binds with the same specificity to identifier sequences that have binding sites. This reduces the probability of not detecting a signal from an identifier sequence due to differences between binding affinities of different compounds. If the number and nature of binding sites are identical between signal emitting identifier sequences (e.g., those denoted as "1"), then each sequence has the same probability of being bound and emitting signal.

Some of the afore-mentioned compounds are inherently detectable such as Hoechst 33258, chromomycin A3 (CMA) and mithramycin A (MMA). Other compounds however must be conjugated to a label in order to be detectable. As will be described in greater detail herein, the label may be a directly detectable label such as a fluorophore, or it may be an indirectly detectable label such as an enzyme label that catalyzes the production of for example a chromophore or fluorophore product.

The addition of identifier compounds such as those recited above to the nucleic acids of the invention can be prior to, simultaneous with, or following addition of the nucleic acid to the sample being tested for analyte content. That is, the nucleic acid may be labeled before, during or after binding of analyte, provided that the conditions for binding of any of these pairs does not disrupt any of the other binding interactions. In some important embodiments, however, the nucleic acid is provided already bound to the identifier compound. For example, if the identifier compound is an identifier oligonucleotide, then a composite nucleic acid already bound to the oligonucleotide is contacted to the sample.

An analyte capture sequence as used herein refers to a sequence that binds (or is bound by) analyte directly or indirectly. In important embodiments, analyte binding occurs indirectly meaning that the analyte is bound to an analyte-specific binding partner that is bound to the nucleic acid.

The analyte capture sequence generally will have binding sites for analyte adaptor compounds which may be analyte-specific binding partners themselves, or which may be conjugated to analyte-specific binding partners. Analyte adaptor compounds may be nucleic acid binding compounds such as oligonucleotides including triplex forming oligonucleotides and bisPNA, proteins including nucleic acid binding proteins, and polyamides, as described herein for identifier compounds. It is to be understood that the teachings relating to these compounds as identifier compounds apply equally here. The number of binding sites per analyte capture sequence is preferably identical between analyte capture sequences of a given composite nucleic acid, and optionally between analyte capture sequences of different composite nucleic acids.

In the simplest instance, the analyte is a nucleic acid (such as an RNA) and the analyte specific binding partner is an oligonucleotide that binds to both the composite nucleic acid as well as to the analyte. Detection of the analyte may require binding of the analyte to a detectably labeled secondary binding partner such as for example in this instance another oligonucleotide.

An analyte-specific binding partner as used herein is a compound that specifically binds to an analyte. Specifically binding to an analyte means that the binding partner binds preferentially to the analyte of interest rather than other compounds. Its affinity for the analyte of interest may be at least 2-fold, at least 5-fold, at least 10-fold, or more than its affinity for another compound. Binding partners with the greatest differential affinity are preferred in most embodiments. The binding partners can be of any nature including but not limited to nucleic acid (e.g., aptamers), peptide (e.g., antibodies or antigen-binding fragments thereof), carbohydrate, lipid, and the like.

A common form of binding partner is an antibody or an antigen-binding antibody fragment. Antibodies include IgG, IgA, IgM, IgE, IgD as well as antibody variants such as single chain antibodies. Antibody fragments contain an antigen-binding site and thus include but are not limited to Fab and F(ab)$_2$ fragments.

A nucleic acid based binding partner such as an oligonucleotide can be used to recognize and bind DNA or RNA based analytes. The nucleic acid based binding partner can be DNA, RNA, LNA or PNA, although it is not so limited. It can also be a combination of one or more of these elements and/or can comprise other nucleic acid mimics.

Binding partners can be primary or secondary. Primary binding partners are those bound to the composite nucleic acid (whether directly or indirectly). Primary binding partners generally are not detectably labeled. Secondary binding partners are those that bind to an analyte that is already bound to the primary binding partner. Preferably, the primary and secondary binding partners bind to different regions on an analyte, unless such sites are repeatedly present on the analyte. In other words, binding of either the primary or secondary binding partner should not effectively compete with or interfere with the binding of the other to the analyte. It is to be understood that in some embodiments the analyte may itself be detectable and there is therefore no need for a secondary binding partner. However, if used, generally only the secondary analyte-specific binding partners are detectably labeled. Preferably, every labeled binding partner has multiple labels conjugated thereto in order to increase signal.

The timing of addition of the secondary binding partner to the sample can vary. For example, it may be added prior to, simultaneously with, or following addition of the composite nucleic acid to the sample.

In instances where a secondary binding partner is used to detect analyte, all secondary binding partners can be conjugated to the same detectable label regardless of their analyte-specificity. This is because such a label merely indicates that the analyte is bound to the nucleic acid, while the signal from the identifier sequence indicates the exact identity of the bound analyte. This eliminates the need for a variety of labels, each specific for a different analyte. It should be understood however that the detectable label bound to the identifier sequence must be different from the detectable label bound to the analyte capture sequence.

It is to be understood that preferably the analyte capture sequence and the mode of analyte capture will be uniform for a given composite nucleic acid. This ensures that all analyte capture sequences have the same probability of binding analyte. This is particularly important if the composite nucleic acids are used to quantitate analyte levels within a sample.

In some important embodiments, the composite nucleic acid is provided already bound to the analyte adaptor compound and if applicable the primary analyte binding partner. For example, if the analyte adaptor compound is an analyte adaptor oligonucleotide, then the oligonucleotide can be bound to the composite nucleic acid and that complex can be contacted with the sample.

Non-specific spacer sequences are nucleic acid sequences that do not interfere with any of the binding interactions necessary to either bind analyte to the composite nucleic acid or to determine the analyte identity. Accordingly, the non-specific spacer sequences are specifically selected or synthesized to lack binding sites for identifier compounds and analyte adaptor compounds. In one embodiment, where particular bisPNA are used as identifier oligonucleotides and analyte adaptor oligonucleotides, it has been found according to the invention that genomic DNA from *Autographa californica* can be used as non-specific spacer sequence since it lacks binding sites of the particular bisPNA used. One of ordinary skill in the art will be able to select, synthesize and/or modify nucleic acids in order to produce suitable non-specific spacer sequence based on the binding sites chosen for the identifier and analyte capture sequences.

The non-specific spacer sequence can exist as a single continuous region along the length of a nucleic acid segment, or it can be divided into, for example, two or three or more regions that are interspersed with identifier and/or analyte capture sequences. The various regions of non-specific spacer sequence can be of any length, and need not be uniform within a segment. However, as stated herein, the location of identifier sequences (and optionally analyte capture sequences) between segments and thus along the length of a composite preferably is uniform, as this facilitates analysis of the composite nucleic acid.

The non-specific spacer sequence length can vary provided the distance between identifier sequences of adjacent segments approximates or exceeds the resolution limit, particularly where adjacent identifier sequences comprise binding sites for identifier compounds (and thus are potentially signal emitting).

Figure 2:
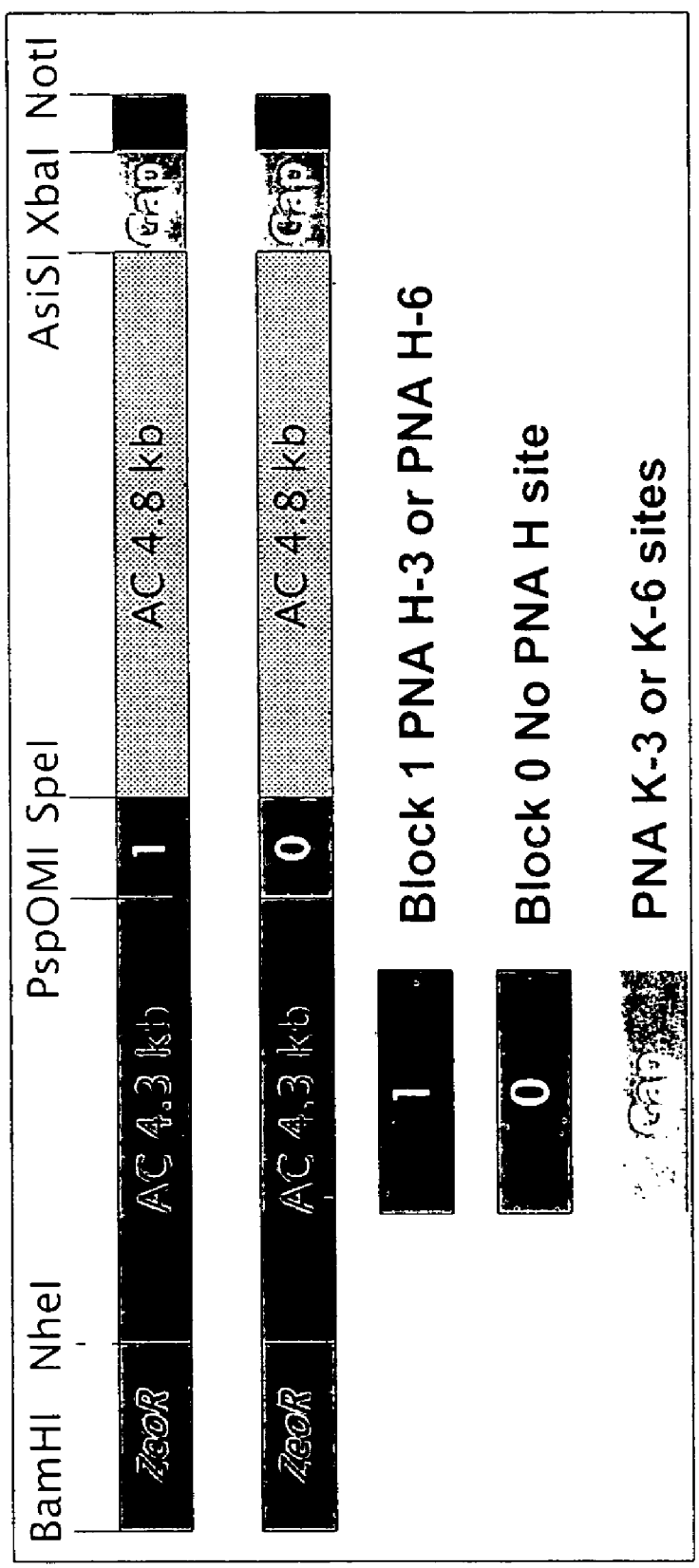
FIG. 2 illustrates additional nucleic acid segments including restriction sites used for generation of the segments. The identifier sequences are denoted by "1" or "0"; the analyte capture sequences are denoted by "Gap"; the non-specific spacer sequence is denoted as "AC".
Figure 3:
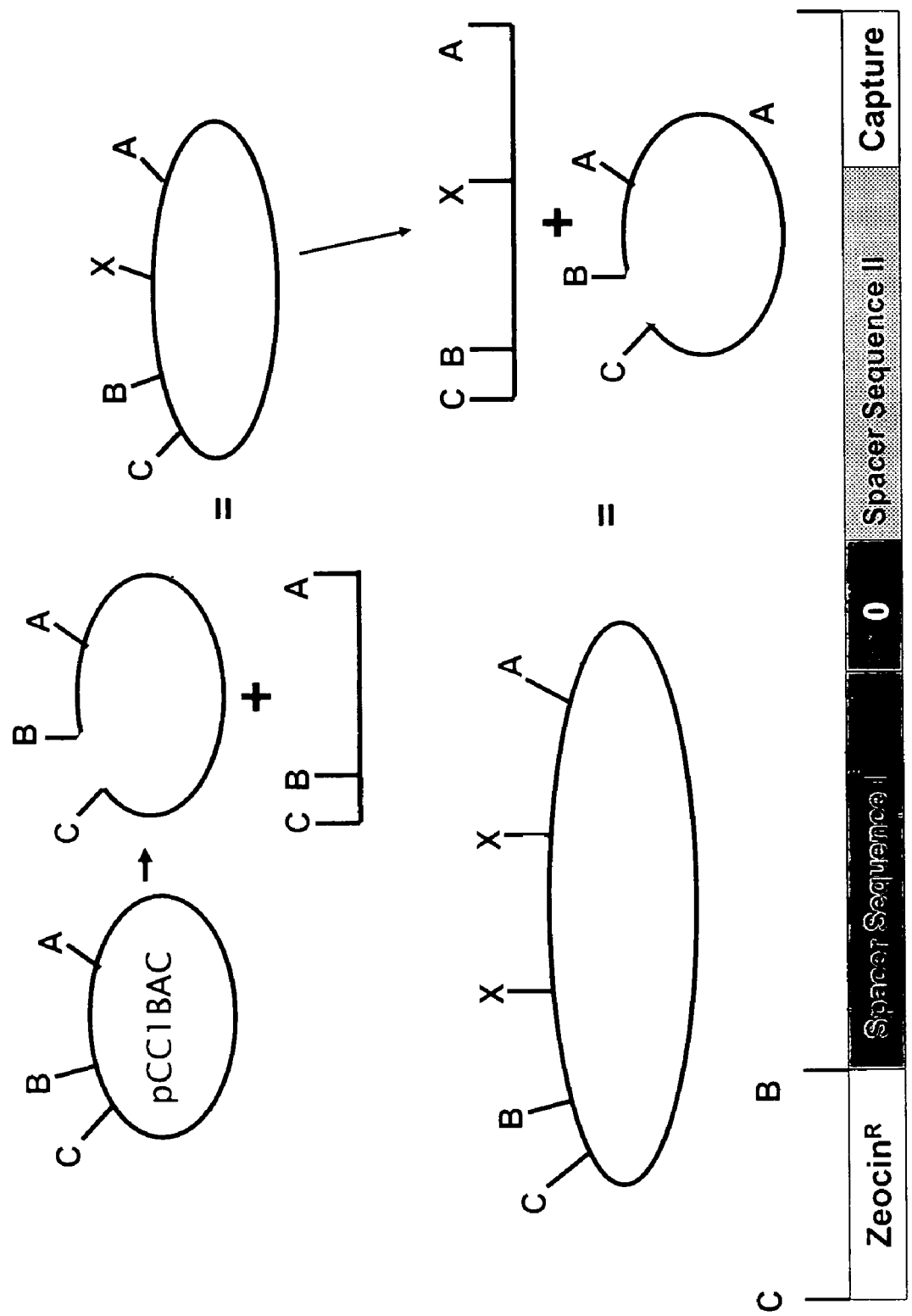
FIG. 3 illustrates a construction strategy for composite nucleic acids (i.e., "Digital DNA™"). The strategy involves iterative cycles of ligating at least one (and preferably more) nucleic acid segments back into a plasmid containing at least one (and preferably more) nucleic acid segments. Sites B and A contain cohesive ends that destroy both sites upon ligation to each other.

For selection and generation purposes, the non-specific spacer sequences may comprise a selection marker such as Zeocin resistance, as shown in FIGS. 2 and 3, and such sequences may be removed during assembly of the segments into composite nucleic acids.

Synthesis of nucleic acid segments and composite nucleic acids can be carried out in a number of ways. The Examples describe particular methodologies for segment and composite synthesis but these are not limiting. Segments can be synthesized by cloning as described in the Examples. Composites can be synthesized by directional cloning such as the iterative cloning shown in FIG. 3. This method can be used to add segment monomers or to add segment multimers to a composite nucleic acid. Composites can also be synthesized using combinations of methods and techniques including directional cloning and homologous recombination, for example, using recombination systems such as Cre/LoxP (shown in FIG. 8). Another example of composite synthesis is shown in FIG. 9.

It may be preferable in some instances to ligate, for example in vitro, two segments to each other, followed by ligation of the segment dimer to another segment monomer to form a segment trimer, followed by iterative ligation of segment monomers. The initial ligations may be performed in vitro, and the later monomer additions can be done by cloning in large capacity vectors such as pCC1BAC, as shown in FIG. 3. The invention also contemplates synthesis, for example by ligation in vitro, of 2 segment dimers which are then ligated to each other to form a segment tetramer. Two segment tetramers can then be linked to each other using for example a homologous recombination system such as the Cre/LoxP system to form 8-mers. These 8-mers may be further homologously recombined to form 16-mers. A similar strategy can be used starting with 5-mers that are recombined to form 10-mers, that are in turn recombined to form 20-mers. Any recombination system that uses Holiday junctions can be used as the invention is not limited in this regard. Another example of such as system is the Flp recombinase system. In this way, "cassettes" with particular sequences of 1's and 0's can be combined in various ways in order to arrive at a desired composite. The use of segment multimers reduces the time required to synthesize the composite.

Figure 6:
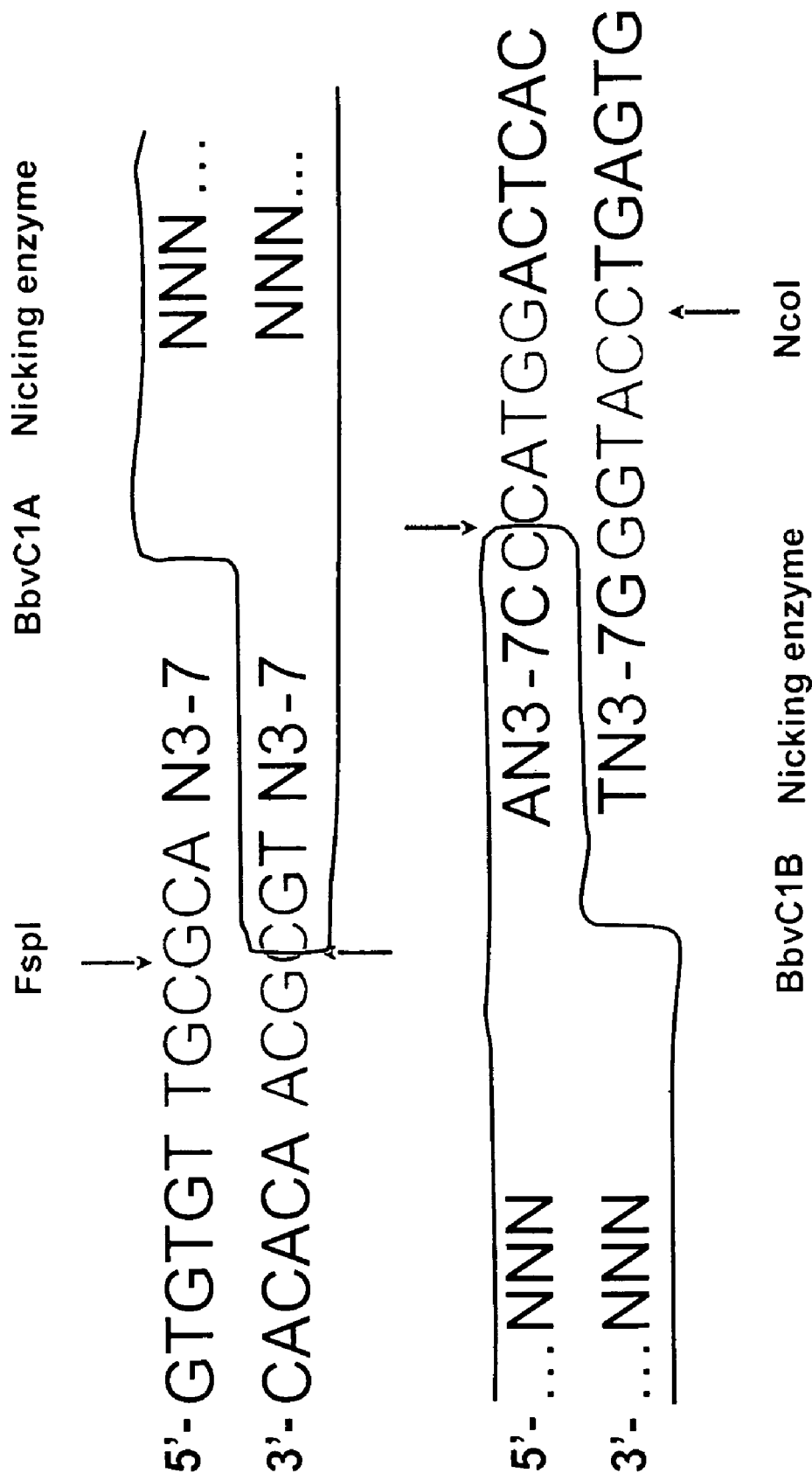
FIG. 6 illustrates the selective 5' and 3' overhangs that can be created using nicking enzymes. These specific overhangs are then used for non-random arrangement of nucleic acid segments. The sequences shown correspond to SEQ ID NOs: 3 and 4.
Figure 7:
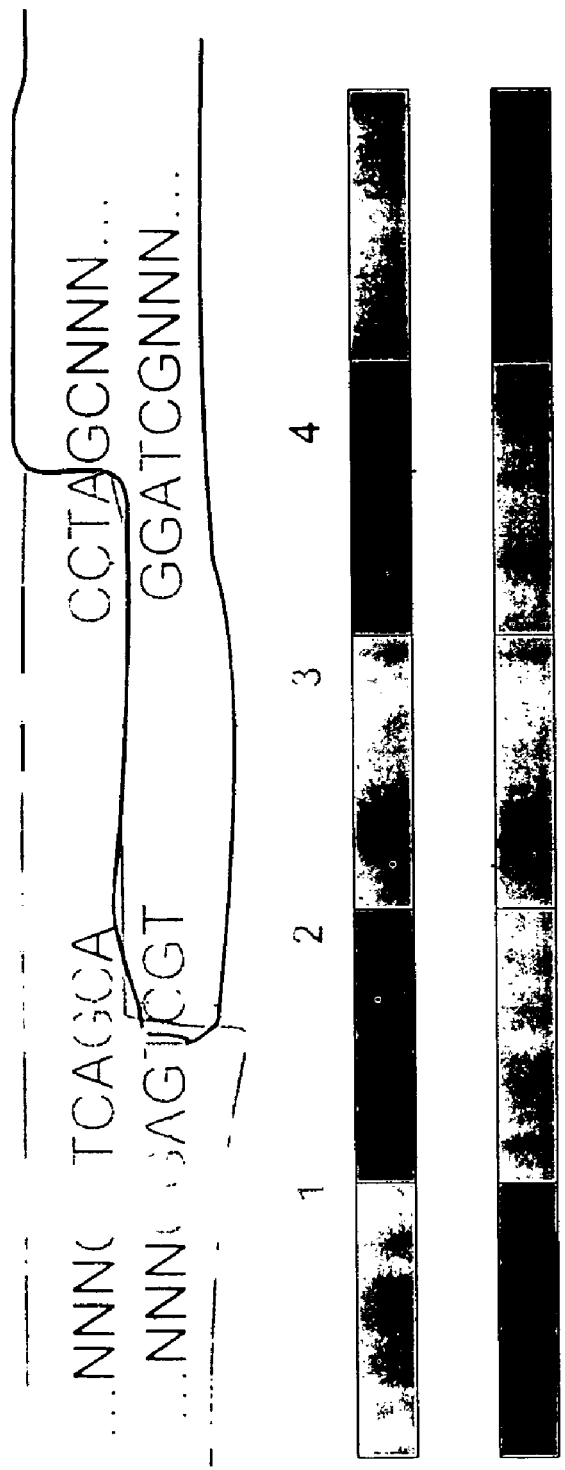
FIG. 7 illustrates the use of nicking enzymes to create selective 5' and 3' overhangs. Different sequence composition of N-stretches between nicking sites creates unique ligation junctions 1, 2, 3 and 4 used for Digital DNA™ assembly. The sequence shown corresponds to SEQ ID NO: 5.

The non-random assembly of nucleic acid segments to form composite nucleic acids in some aspects requires segments having unique 5' and 3' sequence overhangs. One way of achieving such ends employs nicking enzymes. These enzymes create single stranded nicks in double stranded nucleic acids at specific sites. These sites however also encompass some sequence flexibility, as shown for example in FIGS. 6 and 7. This sequence flexibility allows for unique sequence to be incorporated into the ends of nucleic acid segments. These unique sequences in turn are used to directionally assemble segments in a non-random manner. Examples of suitable nicking enzymes include BbvCIA, BbvCIB, BstNBI, and A1WI. Nicking enzymes are available from commercial suppliers such as New England Biolabs. The recognition and cleavage sites of such enzymes are known and available by reference to for example commercial supplier catalogs.

The nucleic acids of the invention can be incorporated into a vector, either as part of their synthesis or when synthesis is complete. The vector is preferably a cloning vector. Examples of such vectors are discussed herein and are known in the art. They generally comprise at least polylinkers for cloning, and selection markers such as antibiotic resistance genes. They may further comprise an origin of replication. A variety of cloning vectors are commercially available, and their sequences are readily available from such commercial sources.

The nucleic acids and vectors can be introduced into cells such as bacterial or eukaryotic cells. The nature of the cell will be generally be determined by the vector used. Laboratory cell lines can be used and these lines are commercially available.

The term "nucleic acid" refers to multiple linked nucleotides (i.e., molecules comprising a sugar (e.g., ribose or deoxyribose) linked to an exchangeable organic base, which is either a pyrimidine (e.g., cytosine (C), thymidine (T) or uracil (U)) or a purine (e.g., adenine (A) or guanine (G)). "Nucleic acid" and "nucleic acid molecule" are used interchangeably and refer to oligoribonucleotides as well as oligodeoxyribonucleotides. The terms shall also include polynucleosides (i.e., a polynucleotide minus a phosphate) and any other organic base containing nucleic acid. The organic bases include adenine, uracil, guanine, thymine, cytosine and inosine. The nucleic acids may be single or double stranded. The nucleic acid may be naturally or non-naturally occurring. Nucleic acids can be obtained from natural sources, or can be synthesized using a nucleic acid synthesizer (i.e., synthetic). Harvest and isolation of nucleic acids are routinely performed in the art and suitable methods can be found in standard molecular biology textbooks. (See, for example, Maniatis' Handbook of Molecular Biology.) The nucleic acid may be DNA or RNA, such as genomic DNA, mitochondrial DNA, mRNA, cDNA, rRNA, miRNA, PNA or LNA, or a combination thereof, as described herein. Non-naturally occurring nucleic acids such as bacterial artificial chromosomes (BACs) and yeast artificial chromosomes (YACs) can also be used.

The invention also contemplates the use of nucleic acid derivatives as the nucleic acid segments, the composite nucleic acids, and/or the oligonucleotides bound thereto. As will be described herein, the use of certain nucleic acid derivatives may increase the stability of the nucleic acids of the invention by preventing their digestion, particularly when they are exposed to biological samples that may contain nucleases.

As used herein, a nucleic acid derivative is a non-naturally occurring nucleic acid or a unit thereof. Nucleic acid derivatives may contain non-naturally occurring elements such as non-naturally occurring nucleotides and non-naturally occurring backbone linkages.

Nucleic acid derivatives may contain backbone modifications such as but not limited to phosphorothioate linkages, phosphodiester modified nucleic acids, combinations of phosphodiester and phosphorothioate nucleic acid, methylphosphonate, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof. The backbone composition of the nucleic acids may be homogeneous or heterogeneous.

Nucleic acid derivatives may contain substitutions or modifications in the sugars and/or bases. For example, they include nucleic acids having backbone sugars which are covalently attached to low molecular weight organic groups other than a hydroxyl group at the 3' position and other than a phosphate group at the 5' position (e.g., an 2'-O-alkylated ribose group). Nucleic acid derivatives may include non-ribose sugars such as arabinose. Nucleic acid derivatives may contain substituted purines and pyrimidines such as C-5 propyne modified bases, 5-methylcytosine, 2-aminopurine, 2-amino-6-chloropurine, 2,6-diaminopurine, hypoxanthine, 2-thiouracil and pseudoisocytosine.

As noted above, the nucleic acid segments, composite nucleic acids and/or oligonucleotides that bind thereto may be composed of peptide nucleic acids (PNA), locked nucleic acid (LNA), DNA, RNA, or co-nucleic acids of the above such as DNA-LNA co-nucleic acids.

PNA are DNA analogs having their phosphate backbone replaced with 2-aminoethyl glycine residues linked to nucleotide bases through glycine amino nitrogen and methylenecarbonyl linkers. PNA can bind to both DNA and RNA targets by Watson-Crick base pairing, and in so doing form stronger hybrids than would be possible with DNA or RNA based oligonucleotides.

PNA are synthesized from monomers connected by a peptide bond (Nielsen, P. E. et al. *Peptide Nucleic Acids, Protocols and Applications*, Norfolk: Horizon Scientific Press, p. 1-19 (1999)). They can be built with standard solid phase peptide synthesis technology. PNA chemistry and synthesis allows for inclusion of amino acids and polypeptide sequences in the PNA design. For example, lysine residues can be used to introduce positive charges in the PNA backbone. All chemical approaches available for the modifications of amino acid side chains are directly applicable to PNA.

PNA has a charge-neutral backbone, and this attribute leads to fast hybridization rates of PNA to DNA. The hybridization rate can be further increased by introducing positive charges in the PNA structure, such as in the PNA backbone or by addition of amino acids with positively charged side chains (e.g., lysines). PNA can form a stable hybrid with DNA molecule. The stability of such a hybrid is essentially independent of the ionic strength of its environment (Orum, H. et al., *BioTechniques* 19(3):472-480 (1995)), most probably due to the uncharged nature of PNAs. This provides PNA with the versatility of being used in vivo or in vitro. However, the rate of hybridization of PNA that include positive charges is dependent on ionic strength, and thus is lower in the presence of salt.

Several types of PNA designs exist, and these include single strand PNA (ssPNA), bisPNA and pseudocomplementary PNA (pcPNA).

The structure of PNA/DNA complex depends on the particular PNA and its sequence. ssPNA binds to single stranded DNA (ssDNA) preferably in antiparallel orientation (i.e., with the N-terminus of the ssPNA aligned with the 3' terminus of the ssDNA) and with a Watson-Crick pairing. PNA also can bind to DNA with a Hoogsteen base pairing, and thereby forms triplexes with double stranded DNA (dsDNA) (Wittung, P. et al., *Biochemistry* 36:7973 (1997)).

ssPNA is the simplest of the PNA molecules. This PNA form interacts with nucleic acids to form a hybrid duplex via Watson-Crick base pairing. The duplex has different spatial structure and higher stability than dsDNA. However, when different concentration ratios are used and/or in presence of complimentary DNA strand, PNA/DNA/PNA or PNA/DNA/DNA triplexes can also be formed (Wittung, P. et al., *Biochemistry* 36:7973 (1997)). The formation of duplexes or triplexes additionally depends upon the sequence of the PNA. Thymine-rich homopyrimidine ssPNA forms PNA/DNA/PNA triplexes with dsDNA targets where one PNA strand is involved in Watson-Crick antiparallel pairing and the other is involved in parallel Hoogsteen pairing. Cytosine-rich homopyrimidine ssPNA preferably binds through Hoogsteen pairing to dsDNA forming a PNA/DNA/DNA triplex. If the ssPNA sequence is mixed, it invades the dsDNA target, displaces the DNA strand, and forms a Watson-Crick duplex. Polypurine ssPNA also forms triplex PNA/DNA/PNA with reversed Hoogsteen pairing.

BisPNA includes two strands connected with a flexible linker. One strand is designed to hybridize with DNA by a classic Watson-Crick pairing, and the second is designed to hybridize with a Hoogsteen pairing. Its binding site can be short (e.g., 8 bp), but the bisPNA/DNA complex is still stable as it forms a hybrid with twice as many (e.g., a 16 bp) base pairings overall. The bisPNA structure further increases specificity of their binding. As an example, binding to an 8 bp site with a probe having a single base mismatch results in a total of 14 bp rather than 16 bp.

Preferably, bisPNAs have homopyrimidine sequences, and even more preferably, cytosines are protonated to form a Hoogsteen pair to a guanosine. Therefore, bisPNA with thymines and cytosines is capable of hybridization to DNA only at pH below 6.5. The first restriction—homopyrimidine sequence only—is inherent to the mode of bisPNA binding. Pseudoisocytosine (J) can be used in the Hoogsteen strand instead of cytosine to allow its hybridization through a broad pH range (Kuhn, H., *J. Mol. Biol.* 286:1337-1345 1999)).

pcPNA involves two single stranded PNAs added to dsDNA (Izvolsky, K. I. et al., *Biochemistry* 10908-10913 (2000)). One pcPNA strand is complementary to the target sequence, while the other is complementary to the displaced DNA strand. As the PNA/DNA duplex is more stable, the displaced DNA generally does not restore the dsDNA structure. The PNA/PNA duplex is more stable than the DNA/PNA duplex and the PNA components are self-complementary because they are designed against complementary DNA sequences. Hence, the added PNAs would rather hybridize to each other. To prevent the self-hybridization of pcPNA units, modified bases are used for their synthesis including 2,6-diamiopurine (D) instead of adenine and 2-thiouracil ($^S$U) instead of thymine. While D and $^S$U are still capable of hybridization with T and A respectively, their self-hybridization is sterically prohibited.

A locked nucleic acid (LNA) is a modified RNA nucleotide. An LNA form hybrids with DNA, which are at least as stable as PNA/DNA hybrids (Braasch, D. A. et al., *Chem & Biol.* 8(1):1-7(2001)). Therefore, LNA can be used just as PNA molecules would be. LNA binding efficiency can be increased in some embodiments by adding positive charges to it. LNAs have been reported to have increased binding affinity inherently.

Commercial nucleic acid synthesizers and standard phosphoramidite chemistry are used to make LNAs. Therefore, production of mixed LNA/DNA sequences is as simple as that of mixed PNA/peptide sequences. The stabilization effect of LNA monomers is not an additive effect. The monomer influences conformation of sugar rings of neighboring deoxynucleotides shifting them to more stable configurations (Nielsen, P. E. et al. *Peptide Nucleic Acids, Protocols and Applications*, Norfolk: Horizon Scientific Press, p. 1-19 (1999)). Also, lesser number of LNA residues in the sequence dramatically improves accuracy of the synthesis. Most of biochemical approaches for nucleic acid conjugations are applicable to LNA/DNA constructs.

PNA backbone modifications include peptide and amino acid variations and modifications. The backbone constituents of PNAs may be peptide linkages, or alternatively, they may be non-peptide linkages. Examples include acetyl caps, amino spacers such as 8-amino-3,6-dioxaoctanoic acid (referred to herein as O-linkers), amino acids such as lysine (particularly useful if positive charges are desired in the PNA), and the like. Various PNA modifications are known and oligonucleotides incorporating such modifications are commercially available from sources such as Boston Probes, Inc.

An analyte as used herein is a substance being detected, quantitated or analyzed according to the invention. Analytes can be any substance for which a binding partner is available. In its broadest sense, the analytes can be detected using virtually any molecular recognition system, such as but not limited to antibodies, aptamers, carbohydrates, etc. The analytes can be organic or inorganic in nature, and in important embodiments, they include proteins, peptides, toxins such as microbial toxins, nucleic acids such as DNA, RNA and oligonucleotides, pathogens such as bacteria, viruses, fungi, parasites, mycobacteria, and the like. As an example, in one instance, the analyte is a nucleic acid specific to a particular pathogen. Thus, the presence of nucleic acid analyte is indicative of pathogen presence.

The invention can be applied to the detection and optionally quantitation of any analyte, but most preferably rare analytes which would otherwise be difficult and/or costly to detect.

The analyte may be a biowarfare agent, or a component thereof. These agents can be biological or chemical in nature. Biological biowarfare agents can be classified broadly as pathogens (including spores thereof) or toxins. As used herein, a pathogen (including a spore thereof) is an agent capable of entering a subject such as a human and infecting that subject. Examples of pathogens include infectious agents such bacteria, viruses, fungi, parasites, mycobacteria and the like. Prions may also be considered pathogens to the extent they are thought to be the transmitting agent for CJD and like diseases. As used herein, a toxin is a pathogen-derived agent that causes disease and often death in a subject without also causing an infection. It derives from pathogens and so may be harvested from such pathogens. Alternatively, it may be synthesized apart from pathogen sources. Biowarfare agents may be weaponized (i.e., aerosolized) for maximum spread. Examples of biowarfare agents include those listed and categorized by the CDC.

CDC Category A agents include *Bacillus anthracis* (otherwise known as anthrax), *Clostridium botulinum* and its toxin (causative agent for botulism), *Yersinia pestis* (causative agent for the plague), variola major (causative agent for small pox), *Francisella tularensis* (causative agent for tularemia), and viral hemorrhagic fever causing agents such as filoviruses Ebola and Marburg and arenaviruses such as Lassa, Machupo and Junin.

CDC Category B agents include Brucellosis (*Brucella* species), epsilon toxin of *Clostridium perfringens*, food safety threats such as *Salmonella species, E. coli* and *Shigella*, Glanders (*Burkholderia mallei*), Melioidosis (*Burkholderia pseudomallei*), Psittacosis (*Chlamydia psittaci*), Q fever (*Coxiella burnetii*), ricin toxin (from *Ricinus communis*—castor beans), Staphylococcal enterotoxin B, Typhus fever (*Rickettsia prowazekii*), viral encephalitis (alphaviruses, e.g., Venezuelan equine encephalitis, eastern equine encephalitis, western equine encephalitis), and water safety threats such as e.g., *Vibrio cholerae, Cryptosporidium parvum*.

CDC Category C agents include emerging infectious diseases such as Nipah virus and hantavirus.

Examples of toxins include abrin, ricin and strychnine. Further examples of toxins include toxins produced by *Corynebacterium diphtheriae* (diphtheria), *Bordetella pertussis* (whooping cough), *Vibrio cholerae* (cholera), *Bacillus anthracis* (anthrax), *Clostridium botulinum* (botulism), *Clostridium tetani* (tetanus), and enterohemorrhagic *Escherichia coli* (bloody diarrhea and hemolytic uremic syndrome), *Staphylococcus aureus* alpha toxin, Shiga toxin (ST), cytotoxic necrotizing factor type 1 (CNF1), *E. coli* heat-stable toxin (ST), botulinum, tetanus neurotoxins, *S. aureus* toxic shock syndrome toxin (TSST), *Aeromonas hydrophila* aerolysin, *Clostridium perfringens* perfringolysin O, *E. coli* hemolysin, *Listeria monocytogenes* listeriolysin O, *Streptococcus pneumoniae* pneumolysin, *Streptococcus pyogenes* streptolysine O, *Pseudomonas aeruginosa* serotoxin A, *E. coli* DNF, *E. coli* LT, *E. coli* CLDT, *E. coli* EAST, *Bacillus anthracis* edema factor, *Bordetella pertussis* dermonecrotic toxin, *Clostridium botulinum* C2 toxin, *C. botulinum* C3 toxin, *Clostridium difficile* toxin A, and *C. difficile* toxin B.

Examples of chemical biowarfare agents that can be detected include arsenic, arsine, benzene, blister agents/vesicants, blood agents, bromine, borombenzylcyanide, chlorine, choking/lung/pulmonary agents, cyanide, distilled mustard, fentanyls and other opioids, mercury, mustard gas, nerve agents, nitrogen mustard, organic solvents, paraquat, phosgene, phosphine, sarin, sesqui mustard, stibine, sulfur mustard, warfarin, tabun, and the like.

The invention can also be used to detect analytes for the purpose of medical diagnoses and/or prognoses. Such analytes also include pathogens such as those listed above. They also include other pathogens including *N. gonorrhea, H. pylori, Staphylococcus* spp., *Streptococcus* spp. such as *Streptococcus pneumoniae, Syphilis*; viruses such as SARS virus, Hepatitis A, B and C viruses, Herpes virus, HIV, West Nile virus, influenza viruses including influenza A virus and bird flu virus, poliovirus, rhinovirus; and parasites such as *Giardia*.

Further examples of bacteria that can be detected include *Pseudomonas* spp., *Clostridium difficile, Legionella* spp., *Pneumococcus* spp., *Haemophilus* spp. (e.g., *Haemophilus influenzae*), *Klebsiella* spp., *Enterobacter* spp., *Citrobacter* spp., *Neisseria* spp. (e.g., *N. meningitidis*), *Shigella* spp., *Salmonella* spp., *Listeria* spp. (e.g., *L. monocytogenes*), *Pasteurella* spp. (e.g., *Pasteurella multocida*), *Streptobacillus* spp., *Spirillum* spp., *Treponema* spp. (e.g., *Treponema pallidum*), *Actinomyces* spp. (e.g., *Actinomyces israelli*), *Borrelia* spp., *Corynebacterium* spp., *Nocardia* spp., *Gardnerella* spp. (e.g., *Gardnerella vaginalis*), *Campylobacter* spp., *Spirochaeta* spp., *Proteus* spp., and *Bacteriodes* spp.

Further examples of viruses that can be detected include Herpes simplex virus 1 and 2 (including encephalitis, neonatal and genital forms), human papilloma virus, cytomegalovirus, Epstein Barr virus, rotavirus, adenovirus, influenza virus, respiratory syncytial virus, varicella-zoster virus, small pox and monkey pox.

Further examples of fungi that can be detected include candidiasis, ringworm, histoplasmosis, blastomycosis, paracoccidioidomycosis, crytococcosis, aspergillosis, chromomycosis, mycetoma, pseudallescheriasis, and tinea versicolor.

Further examples of parasites that can be detected include both protozoa and nematodes such as amebiasis, *Trypanosoma cruzi*, Fascioliasis (e.g., *Facioloa hepatica*), Leishmaniasis, *Plasmodium* (e.g., *P. falciparum, P. knowlesi, P. malariae*,) Onchocerciasis, Paragonimiasis, *Trypanosoma brucei, Pneumocystis* (e.g., *Pneumocystis carinii*), *Trichomonas vaginalis*, Taenia, *Hymenolepsis* (e.g., *Hymenolepsis nana*), Echinococcus, Schistosomiasis (e.g., *Schistosoma mansoni*), neurocysticercosis, *Necator americanus*, and *Trichuris trichuria*.

Further examples of pathogens that can be detected include *Chlamydia, M. tuberculosis* and *M. leprosy*, and Rickettsiae.

The foregoing lists of pathogens are not intended to be exhaustive but rather exemplary.

The invention can also be used to detect bodily cells and/or components thereof. These may also be useful in clinical diagnoses and/or prognoses. These include detection of malignant cells (e.g., to determine whether a cancer is present and/or has metastasized), nucleic acids (e.g., to determine the presence or absence of a particular genetic mutation and/or to diagnose a disease based on such a genetic mutation), and the like.

The sample to be tested for analyte presence and/or amount can be derived from virtually any source and will depend primarily on the analyte being detected. The sample may be a biological sample from a subject such as a bodily fluid or tissue. The term tissue as used herein refers to both localized and disseminated cell populations including but not limited to brain, heart, breast, colon, bladder, uterus, prostate, stomach, testis, ovary, pancreas, pituitary gland, adrenal gland, thyroid gland, salivary gland, mammary gland, kidney, liver, intestine, spleen, thymus, bone marrow, trachea and lung. Biological fluids include saliva, sperm, serum, plasma, blood, lymph and urine, but are not so limited. Both invasive and non-invasive techniques can be used to obtain such samples and these are known to those of ordinary skill in the art.

Alternatively, the sample may be an environmental sample such as but not limited to an air sample or a water sample. In this latter embodiment, the sample may be checked for, for example, chemical or biological warfare agents such as those recited herein. If the sample is an air sample, it will generally require dissolution in a liquid base such as a buffered solution. This is usually also the case with solid samples.

The analyte being detected can dictate whether the sample needs to be further manipulated prior to analysis. In some embodiments, it may be necessary to disrupt tissue or cells (including intact pathogens) prior to contact with the nucleic acids of the invention. Disruption can be mechanical, including acoustic disruption (e.g., ultrasound based disruption), and may be carried out to varying degrees. For example, a sample may be disrupted to the point of rupturing cell walls and/or cell membranes and releasing cell wall fragments, intracellular organelles, proteins, lipids, RNA and/or genomic DNA, all of which may be analytes.

Depending on the expected concentration of the analyte being detected, the sample may be diluted or concentrated prior to analysis. Sample dilution will generally involve mixing of the sample with a larger volume of solute. Sample concentration can be accomplished in a number of ways known in the art including but not limited to gravity, centrifugation, filtering, and the like. Concentration may also be accomplished using flow-based concentration methods. These latter methods are described in greater detail in published PCT Patent Application WO 2006/017274.

The invention can be used to determine the presence or absence of an analyte in a sample and also, in some instances, the concentration or absolute amount of the analyte. The analyte-specific binding partners may be those present on a single composite nucleic acid, or alternatively the sum of all binding partners present on all composite nucleic acids of identical specificity used in the analysis. As will be understood by those of ordinary skill, each composite nucleic acid (or each plurality of composites having the same analyte specificity) must present enough analyte-specific binding partners to enable a wide range of analyte concentrations to be detected. In other words, the number of analyte-specific binding partners must be greater than the number of analytes in the sample so as not to be saturated.

Concentration is determined by measuring the amount of analyte signal bound to (or emitted from) the composite nucleic acid or the plurality of composites having the same analyte specificity. Analyte signal refers to signal from for example secondary binding partners that are bound to the composite by virtue of binding to the analyte. This signal is distinguishable from signal from the identifier sequences.

If the analyte concentration in the sample is very high, the sample can be diluted in order to quantitate analyte concentration accurately. If the analyte concentration is low, the sample may be concentrated.

The signal level can be compared to a standard calibration curve that is prepared prior to or at the same time as the sample is analyzed. The standard calibration curve may be a plot of signal intensity (y-axis) as a function of analyte concentration α-axis). Those of ordinary skill will be familiar with the generation of such curves.

The incubation time and conditions required for binding of analyte to analyte binding partners will be dictated by the particular analyte and the binding affinity of the analyte binding partner(s). One of ordinary skill in the art is capable of determining these parameters.

The sample may be analyzed using a single linear polymer analysis system such as but not limited to GeneEngine™. When placed in a moving fluid, nucleic acid is stretched in a microfluidic chip of the GeneEngine™ and translocated into an interrogation channel. Once in the interrogation channel, stretched nucleic acid passes through the interrogation zone (e.g., a spot of excitation light). In some embodiments, the spot diameter is about 0.5 µm, and therefore much smaller than the stretched DNA length which is about 34 µm for 100 kb DNA.

In one embodiment, the GeneEngine™ platform is used with focusing flow design, as described in published US patent applications US20050112606A1 and published PCT patent application WO 2006/017274. This arrangement provides interrogation of all nucleic acids, improves nucleic acid stretching, and moves the sample through the center of the excitation beam for more efficient detection. This arrangement therefore increases signal to noise (S/N) ratio and minimizes dispersion of excitation power.

Using such flow configurations, it is also possible to concentrate and/or redirect polymers of interest, such as nucleic acids having an analyte of interest bound thereto. In a flow system, this is easily accomplished by redirecting flow into a collection vessel. The collected nucleic acid can then be manipulated, possibly to dissociate the analyte from its respective binding partner(s). The analyte whether in free or bound form can then be analyzed in greater detail. For example, if the analyte is a nucleic acid, it may be analyzed via PCR.

Various compounds described herein may be labeled including for example identifier compounds such as oligonucleotides, secondary analyte binding partners such as secondary antibodies, and the composite nucleic acid.

Detectable labels such as fluorophores can be directly incorporated into nucleic acids during their synthesis, or they can be conjugated to the nucleic acid following synthesis. There are several known methods of direct chemical labeling of DNA (Hermanson, G. T., Bioconjugate Techniques, Academic Press, Inc., San Diego, 1996; Roget et al., NAR 17(19): 7043-51, 1989; Proudnikov and Mirzabekov, NAR 24(22): 4535-42, 1996). Nucleic acids can also be synthesized de novo (e.g., using automated nucleic acid synthesizers) using fluorescently labeled nucleotides. Such nucleotides are commercially available from suppliers such as Amersham Pharmacia Biotech, Molecular Probes, and New England Nuclear/Perkin Elmer.

A detectable label is a moiety, the presence of which can be ascertained directly or indirectly. The label may be of a chemical, peptide or nucleic acid nature although it is not so limited. The nature of label used will depend on a variety of factors, including the nature of the analysis being conducted, the type of the energy source and detector used, and the type of nucleic acid, analyte, oligonucleotides and primary, secondary analyte-specific binding partners, and the like. The label should be sterically and chemically compatible with the constituents to which it is bound.

Detection of the label generally requires generation and detection of a signal such as for example an emission of energy. The label can be detected directly for example by its ability to emit and/or absorb electromagnetic radiation of a particular wavelength. A label can be detected indirectly for example by its ability to bind, recruit and, in some cases, cleave another moiety which itself may emit or absorb light of a particular wavelength (e.g., an epitope tag such as the FLAG epitope, an enzyme tag such as horseradish peroxidase, etc.).

The detectable label can be but is not limited to directly detectable labels such as a fluorescent molecule (e.g., POPO-1, TOTO-3, TAMRA, Alexa 546, Alexa 647, fluorescein, rhodamine, tetramethylrhodamine, R-phycoerythrin, Cy-3, Cy-5, Cy-7, Texas Red, Phar-Red, allophycocyanin (APC), fluorescein amine, eosin, dansyl, umbelliferone, 5-carboxyfluorescein (FAM), 2'7'-dimethoxy-4'5'-dichloro-6-carboxyfluorescein (JOE), 6 carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), 5-(2'-aminoethyl) aminonaphthalene-1-sulfonic acid (EDANS), 4-acetamido-4'-isothiocyanatostilbene-2,2'disulfonic acid, acridine, acridine isothiocyanate, r-amino-N-(3-vinylsulfonyl)phenylnaphthalimide-3,5, disulfonate (Lucifer Yellow VS), N-(4-anilino-1-naphthyl)maleimide, anthranilamide, Brilliant Yellow, coumarin, 7-amino-4-methylcoumarin, 7-amino-4-trifluoromethylcouluarin (Coumarin 151), cyanosine, 4',6-diaminidino-2-phenylindole (DAPI), 5',5"-diaminidino-2-phenylindole (DAPI), 5',5"-dibromopyrogallol-sulfonephthalein (Bromopyrogallol Red), 7-diethylamino-3-(4'-isothiocyanatophenyl)-4-methylcoumarin diethylenetriamine pentaacetate, 4,4'-diisothiocyanatodihydro-stilbene-2,2'-disulfonic acid, 4,4'-diisothiocyanatostilbene-2,2'-disulfonic acid, 4-dimethylaminophenylazophenyl-4'-isothiocyanate (DABITC), eosin isothiocyanate, erythrosin B, erythrosin isothiocyanate, ethidium, 5-(4,6-dichlorotriazin-2-yl) aminofluorescein (DTAF), QFITC (XRITC), fluorescamine, IR144, IR1446, Malachite Green isothiocyanate, 4-methylumbelliferone, ortho cresolphthalein, nitrotyrosine, pararosaniline, Phenol Red, B-phycoerythrin, o-phthaldialdehyde, pyrene, pyrene butyrate, succinimidyl 1-pyrene butyrate, Reactive Red 4 (Cibacron® Brilliant Red 3B-A), lissamine rhodamine B sulfonyl chloride, rhodamine B, rhodamine 123, rhodamine X, sulforhodamine B, sulforhodamine 101, sulfonyl chloride derivative of sulforhodamine 101, tetramethyl rhodamine, riboflavin, rosolic acid, and terbium chelate derivatives), a chemiluminescent molecule, a bioluminescent molecule, a chromogenic molecule, a radioisotope (e.g., $P^{32}$ or $H^3$, $^{14}C$, $^{125}I$ and $^{131}I$), an electron spin resonance molecule (such as for example nitroxyl radicals), an optical or electron density molecule, an electrical charge transducing or transferring molecule, an electromagnetic molecule such as a magnetic or paramagnetic bead or particle, a semiconductor nanocrystal or nanoparticle (such as quantum dots described for example in U.S. Pat. No. 6,207,392 and commercially available from Quantum Dot Corporation and Evident Technologies), fluorescently labeled microspheres (e.g., commercially available from Invitrogen), a colloidal metal, a colloid gold nanocrystal, a nuclear magnetic resonance molecule, and the like.

The detectable label can also be but is not limited to indirectly detectable labels such as an enzyme (e.g., alkaline phosphatase, horseradish peroxidase, β-galactosidase, glucoamylase, lysozyme, luciferases such as firefly luciferase and bacterial luciferase (U.S. Pat. No. 4,737,456); saccharide oxidases such as glucose oxidase, galactose oxidase, and glucose-6-phosphate dehydrogenase; heterocyclic oxidases such as uricase and xanthine oxidase coupled to an enzyme that uses hydrogen peroxide to oxidize a dye precursor such as HRP, lactoperoxidase, or microperoxidase), an enzyme substrate, and the like.

Labels may be bound (either covalently or non-covalently) to a compound of interest via an affinity molecule, a ligand, a receptor, a biotin molecule, an avidin (including streptavidin) molecule, an antigen (e.g., epitope tags such as the FLAG or HA epitope), a hapten (e.g., biotin, pyridoxal, digoxigenin fluorescein and dinitrophenol), an antibody, an antibody fragment, a microbead, and the like. Antibody fragments include Fab, F(ab)$_2$, Fd and antibody fragments which include a CDR3 region.

In some embodiments, some of the binding pairs are labeled with donor and acceptor fluorophores. For example, primary and secondary analyte-specific binding partners may be conjugated with donor and acceptor fluorophores that form a FRET (fluorescence resonance energy transfer) pair. In this case, a blue laser light may be used to excite fluorescence of donor fluorophores. A portion of the energy absorbed by the donors is transferred to acceptor fluorophores if they are spatially close enough to the donor molecules (i.e., the distance between them must approximate or be less than the Forster radius or the energy transfer radius). Once the acceptor fluorophore absorbs the energy, it in turn fluoresces in its characteristic emission wavelength. Since energy transfer is possible only when the acceptor and donor are located in close proximity, acceptor fluorescence is unlikely if the secondary analyte-specific binding partner is not bound to the analyte which is in turn bound to the primary analyte-specific binding partner. Acceptor fluorescence therefore can be used to determine presence and optionally concentration of analyte.

In another embodiment, an analyte such as an miRNA could be labeled with a FRET pair member and the analyte adapter compound, which could be an oligonucleotide, could be labeled with the respective FRET pair member.

FRET fluorophore pairs are two fluorophores that are capable of undergoing FRET to produce or eliminate a detectable signal when positioned in proximity to one another. Examples of FRET donors include Alexa 488, Alexa 546, BODIPY 493, Oyster 556, Fluor (FAM), Cy3 and TMR (TAMRA). Examples of FRET acceptors include Cy5, Alexa 594, Alexa 647 and Oyster 656. Cy5 can work as a donor with Cy3, TMR or Alexa 546, as an example.

FRET alone generally requires only one excitation source (and thus wavelength) and sometimes only one detector. The detector may be set to either the emission spectrum of the donor or acceptor fluorophore. It is set to the donor fluorophore emission spectrum if FRET is detected by quenching of donor fluorescence. Alternatively, it is set to the acceptor fluorophore emission spectrum if FRET is detected by acceptor fluorophore emission. In some embodiments, FRET emissions of both donor and acceptor fluorophores can be detected. In still other embodiments, the donor is excited with polarized light and polarization of both emission spectra is detected.

In a preferred embodiment, every analyte-specific binding partner that is to be directly detected is conjugated with many of the same detectable label (e.g., fluorophores). Multiple labels result in stronger fluorescence signals, greater signal to noise ratios, and thus better detection.

The nucleic acid may be labeled in a sequence-independent manner in addition to the sequence-dependent manner described herein. Sequence-independent labeling preferably results in relatively uniform labeling of the nucleic acid along its length. This is useful for confirming that any detected signals are associated with a composite nucleic acid rather with unbound label. The sequence-independent labeling can also be used to indicate the beginning and end of a composite being analyzed, and thus points in between.

Sequence-independent labeling can be achieved using a backbone stain or label. Examples of backbone stains include intercalating dyes such as phenanthridines and acridines (e.g., ethidium bromide, propidium iodide, hexidium iodide, dihydroethidium, ethidium homodimer-1 and -2, ethidium monoazide, and ACMA); minor grove binders such as indoles and imidazoles (e.g., Hoechst 33258, Hoechst 33342, Hoechst 34580 and DAPI); and miscellaneous nucleic acid stains such as acridine orange (also capable of intercalating), 7-AAD, actinomycin D, LDS751, and hydroxystilbamidine. All of the aforementioned nucleic acid stains are commercially available from suppliers such as Molecular Probes, Inc.

Still other examples of nucleic acid stains include the following dyes from Molecular Probes: cyanine dyes such as SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red).

Thus, in some instances, the composite nucleic acids will emit a number of signals including a backbone stain signal, an identifier compound signal, and an analyte signal such as a secondary analyte binding partner signal. The detection system should be capable of detecting and distinguishing between these distinct signals. Such a system should be equipped for three color detection and possibly three color excitation. If the FRET configuration is used as described herein, then the number of excitation lasers and/or detectors may be reduced.

As an example, in one embodiment, three different lasers are used for excitation at the following wavelengths: 488 nm (blue), 532 nm (green), and 633 nm (red). These lasers excite fluorescence of Alexa 488, TMR (tetramethylrhodamine, TAMRA), and TOTO-3 fluorophores, respectively. Fluorescence from all these fluorophores can be detected independently. As an example of fluorescence strategy, the identifier compounds may be labeled with Alexa 488 fluorophores, the secondary analyte specific binding partners may be labeled with TMR, and the nucleic acid backbone may be labeled with TOTO-3. TOTO-3 is an intercalating dye that non-specifically stains DNA in a length-proportional manner. In this configuration, Alexa 488 fluorescence is used to determine the barcode or labeling pattern of the nucleic acid (and thus the analyte identity), TMR fluorescence is indicative of analyte presence in the sample, and TOTO-3 fluorescence provides context for the barcode signal by labeling part of or the entire length of the nucleic acid, in some instances thereby allowing fine tuning of the barcode. TMR fluorescence can also be used to quantitate analyte concentration in the solution, as discussed herein. Another suitable set of fluorophores that can be used is the combination of POPO-1, TMR and Alexa 647 (or Cy5) which are excited by 442, 532 and 633 nm lasers respectively.

As used herein, "conjugated" means two entities stably bound to one another by any physicochemical means. It is important that the nature of the attachment is such that it does not substantially impair the effectiveness of either entity. Keeping these parameters in mind, any covalent or non-covalent linkage known to those of ordinary skill in the art is contemplated unless explicitly stated otherwise herein. Non-covalent conjugation includes hydrophobic interactions, ionic interactions, high affinity interactions such as biotin-avidin and biotin-streptavidin complexation and other affinity interactions. Such means and methods of attachment are known to those of ordinary skill in the art. Conjugation can be performed using standard techniques common to those of ordinary skill in the art. For example, U.S. Pat. Nos. 3,940,475 and 3,645,090 demonstrate conjugation of fluorophores and enzymes to antibodies.

The various components described herein can be conjugated to each other by any mechanism known in the art. For instance, functional groups which are reactive with various labels include, but are not limited to, (functional group: reactive group of light emissive compound) activated ester:amines or anilines; acyl azide:amines or anilines; acyl halide: amines, anilines, alcohols or phenols; acyl nitrile:alcohols or phenols; aldehyde:amines or anilines; alkyl halide:amines, anilines, alcohols, phenols or thiols; alkyl sulfonate:thiols, alcohols or phenols; anhydride:alcohols, phenols, amines or anilines; aryl halide:thiols; aziridine:thiols or thioethers; carboxylic acid:amines, anilines, alcohols or alkyl halides; diazoalkane:carboxylic acids; epoxide:thiols; haloacetamide: thiols; halotriazine:amines, anilines or phenols; hydrazine: aldehydes or ketones; hydroxyamine:aldehydes or ketones; imido ester:amines or anilines; isocyanate:amines or anilines; and isothiocyanate:amines or anilines.

Analyte capture compounds including those that are non-nucleic acid in nature can be conjugated to the nucleic acid, and the detectable labels can be conjugated to all suitable components of the system, by covalent or non-covalent means, whether directly or indirectly. Linkers and/or spacers may be used in some instances.

Linkers can be any of a variety of molecules, preferably nonactive, such as nucleotides or multiple nucleotides, straight or even branched saturated or unsaturated carbon chains of $C_1$-$C_{30}$, phospholipids, amino acids, and in particular glycine, and the like, whether naturally occurring or synthetic. Additional linkers include alkyl and alkenyl carbonates, carbamates, and carbamides. These are all related and may add polar functionality to the linkers such as the $C_1$-$C_{30}$ previously mentioned. As used herein, the terms linker and spacer are used interchangeably. The length of the spacer can vary depending upon the application and the nature of the components being conjugated (e.g., the nucleic acid and the primary analyte-specific binding partner and the distance that can be tolerated between binding sites on the nucleic acid).

Linkers or spacers may be homo-bifunctional or hetero-bifunctional cross-linkers, depending upon the nature of the molecules to be conjugated. Homo-bifunctional cross-linkers have two identical reactive groups. Hetero-bifunctional cross-linkers are defined as having two different reactive groups that allow for sequential conjugation reaction. Various types of commercially available cross-linkers are reactive with one or more of the following groups: primary amines, secondary amines, sulphydryls, carboxyls, carbonyls and carbohydrates. Examples of amine-specific cross-linkers are bis(sulfosuccinimidyl) suberate, bis[2-(succinimidooxycarbonyloxy)ethyl]sulfone, disuccinimidyl suberate, disuccinimidyl tartarate, dimethyl adipimate-2HCl, dimethyl pimelimidate-2HCl, dimethyl suberimidate-2 HCl, and ethylene glycolbis-[succinimidyl-[succinate]]. Cross-linkers reactive with sulfhydryl groups include bismaleimidohexane, 1,4-di-[3'-(2'-pyridyldithio)-propionamido)]butane, 1-[p-azidosalicylamido]-4-[iodoacetamido]butane, and N-[4-(p-azidosalicylamido) butyl]-3'-[2'-pyridyldithio]propionamide. Cross-linkers preferentially reactive with carbohydrates include azidobenzoyl hydrazine. Cross-linkers preferentially reactive with carboxyl groups include 4-[p-azidosalicylamido]butylamine. Heterobifunctional cross-linkers that react with amines and sulfhydryls include N-succinimidyl-3-[2-pyridyldithio]propionate, succinimidyl[4-iodoacetyl]aminobenzoate, succinimidyl 4-[N-maleimidomethyl]cyclohexane-1-carboxylate, m-maleimidobenzoyl-N-hydroxysuccinimide ester, sulfosuccinimidyl 6-[3-[2-pyridyldithio]propionamido]hexanoate, and sulfosuccinimidyl 4-[N-maleimidomethyl]cyclohexane-1-carboxylate. Heterobifunctional cross-linkers that react with carboxyl and amine groups include 1-ethyl-3-[3-dimethylaminopropyl]-carbodiimide hydrochloride. Heterobifunctional cross-linkers that react with carbohydrates and sulfhydryls include 4-[N-maleimidomethyl]-cyclohexane-1-carboxylhydrazide-2HCl, 4-(4-N-maleimidophenyl)-butyric acid hydrazide 2HCl, and 3-[2-pyridyldithio]propionyl hydrazide. The cross-linkers are bis-[β-4-azidosalicylamido) ethyl]disulfide and glutaraldehyde.

Other cross linkers include psoralen, furocoumarins, benzodipyrones and bis-azides, as described herein.

Amine or thiol groups may be added at any nucleotide of a nucleic acid so as to provide a point of attachment for a bifunctional cross-linker molecule. The nucleic acid may be synthesized incorporating conjugation-competent reagents such as Uni-Link AminoModifier, 3'-DMT-C6-Amine-ON CPG, AminoModifier II, N-TFA-C6-AminoModifier, C6-ThiolModifier, C6-Disulfide Phosphoramidite and C6-Disulfide CPG (Clontech, Palo Alto, Calif.).

A wide variety of spacers can be used, many of which are commercially available, for example, from sources such as Boston Probes, Inc. (now Applied Biosystems). Spacers are not limited to organic spacers, and rather can be inorganic also (e.g., —O—Si—O—, or O—P—O—). Additionally, they can be heterogeneous in nature (e.g., composed of organic and inorganic elements). Essentially, any molecule having the appropriate size restrictions and capable of being linked to the various components such as fluorophore and oligonucleotide can be used as a linker. Examples include the E linker (which also functions as a solubility enhancer), the X linker which is similar to the E linker, the 0 linker which is a glycol linker, and the P linker which includes a primary aromatic amino group (all supplied by Boston Probes, Inc., now Applied Biosystems). Other suitable linkers are acetyl linkers, 4-aminobenzoic acid containing linkers, Fmoc linkers, 4-aminobenzoic acid linkers, 8-amino-3,6-dioxactanoic acid linkers, succinimidyl maleimidyl methyl cyclohexane carboxylate linkers, succinyl linkers, and the like. Another example of a suitable linker is that described by Haralambidis et al. in U.S. Pat. No. 5,525,465, issued on Jun. 11, 1996.

In some instances, it may be desirable to use a linker or spacer comprising a bond that is cleavable under certain conditions. For example, the bond can be one that cleaves under normal physiological conditions or that can be caused to cleave specifically upon application of a stimulus such as light. Readily cleavable bonds include readily hydrolyzable bonds, for example, ester bonds, amide bonds and Schiff's base-type bonds. Bonds which are cleavable by light are known in the art.

The nucleic acids may be analyzed using a single molecule analysis system (e.g., a single polymer analysis system). A single molecule detection system is capable of analyzing individual molecules rather than relying solely on analysis of bulk populations of molecules. Such a system may be capable of analyzing single molecules in a linear manner. In certain embodiments in which detection is based predominately on the presence or absence of a signal, linear analysis may not be required. However, there are other embodiments embraced by the invention which would benefit from the ability to linearly analyze nucleic acids. These include applications in which the nucleic acids are distinguished based on spatial labeling pattern rather than a unique detectable label.

Thus, preferably, the single molecule analysis system is also a linear polymer analysis system. A linear polymer analysis system is a system that analyzes polymers such as nucleic acids, in a linear manner (i.e., starting at one location on the polymer and then proceeding linearly in either direction therefrom). As a polymer is analyzed, the detectable labels attached to it are detected in a sequential manner, whereby a histogram is formed (signal intensity vs. time) that can then be translated into a map, with knowledge of the velocity of the polymer. The system can also detect the labels simultaneously, whereby an image of the polymer is formed, from which distances between labels can be determined. It is to be understood that in some embodiments, the polymer is attached to a solid support, while in others it is free flowing. In either case, the velocity of the polymer as it moves past, for example, an interaction station or a detector, will aid in determining the position of the labels relative to each other and relative to other detectable markers that may be present on the polymer.

In some embodiments, it is preferred that the polymer be flexible. This is the case with nucleic acids, such as DNA which normally exists as a random coil but can be stretched (or elongated) in order to read the barcode. Stretching the polymer while it is being read (i.e., interrogation) enables a higher degree of multiplexing since polymers can be distinguished from each other based on their unique labeling patterns. Stretching is not required however during for example identifier compound or analyte-adaptor compound incubation since the small size of the random coil facilitates faster diffusion rates and therefore reduces incubation time.

The invention further contemplates analysis of nucleic acids in a compact, non-elongated form. This can be useful if each identifier-based labeling is uniquely detected irrespective of spatial location of identifier compounds or detectable labels. For example, it is possible that each composite nucleic acid is labeled with a unique label and the presence of the label regardless of its position along the length of the nucleic acid is used to identify the nucleic acid (and consequently the analyte bound thereto). This approach will be best suited to applications that do not require extensive multiplexing. It should be understood that this approach will therefore not require a linear analysis system nor will it require elongation of the nucleic acid prior to or during interrogation.

An example of a suitable system is the GeneEngine™ (U.S. Genomics, Inc., Woburn, Mass.). The Gene Engine™ system is described in published PCT patent applications WO98/35012 and WO00/09757, published on Aug. 13, 1998, and Feb. 24, 2000, respectively, and in issued U.S. Pat. No. 6,355,420 B1, issued Mar. 12, 2002. This system is both a single molecule analysis system and a linear polymer analysis system. It allows, for example, single nucleic acids to be passed through an interaction station in a linear manner, whereby regions on the nucleic acid are interrogated individually in order to determine whether there is a detectable label conjugated to the nucleic acid. Interrogation involves exposing the nucleic acid to an energy source such as optical radiation of a set wavelength. The mechanism for signal emission and detection will depend on the type of label sought to be detected, as described herein.

This system comprises an optical source for emitting optical radiation; an interaction station for receiving the optical radiation and for receiving a polymer that is exposed to the optical radiation to produce detectable signals; and a processor constructed and arranged to analyze the polymer based on the detected radiation including the signals.

In one embodiment, the interaction station includes a localized radiation spot. In a further embodiment, the system further comprises a microchannel that is constructed to receive and advance the polymer through the localized radiation spot, and which optionally may produce the localized radiation spot. In another embodiment, the system further comprises a polarizer, wherein the optical source includes a laser constructed to emit a beam of radiation and the polarizer is arranged to polarize the beam. While laser beams are intrinsically polarized, certain diode lasers would benefit from the use of a polarizer. In some embodiments, the localized radiation spot is produced using a slit located in the interaction station. The slit may have a slit width in the range of 1 nm to 500 nm, or in the range of 10 nm to 100 nm. In some embodiments, the polarizer is arranged to polarize the beam prior to reaching the slit. In other embodiments, the polarizer is arranged to polarize the beam in parallel to the width of the slit.

In yet another embodiment, the optical source is a light source integrated on a chip. Excitation light may also be delivered using an external fiber or an integrated light guide. In the latter instance, the system would further comprise a secondary light source from an external laser that is delivered to the chip.

The analysis may also comprise generating optical radiation of a known wavelength to produce a localized radiation spot; passing a polymer through a microchannel; irradiating the polymer at the localized radiation spot; sequentially detecting radiation resulting from interaction of the polymer with the optical radiation at the localized radiation spot; and analyzing the polymer based on the detected radiation.

In one embodiment, the method further employs an electric field to pass the polymer through the microchannel. In another embodiment, detecting includes collecting the signals over time while the polymer is passing through the microchannel.

The systems described herein will encompass at least one detection system. The nature of such detection systems will depend upon the nature of the detectable label. The detection system can be selected from any number of detection systems known in the art. These include an electron spin resonance (ESR) detection system, a charge coupled device (CCD) detection system, a fluorescent detection system, an electrical detection system, a photographic film detection system, a chemiluminescent detection system, an enzyme detection system, an atomic force microscopy (AFM) detection system, a scanning tunneling microscopy (STM) detection system, an optical detection system, a nuclear magnetic resonance (NMR) detection system, a near field detection system, and a total internal reflection (TIR) detection system, many of which are electromagnetic detection systems.

Other single molecule nucleic acid analytical methods which involve elongation of DNA molecules can also be used in the methods of the invention. These include fiber-fluorescence in situ hybridization (fiber-FISH) (Bensimon, A. et al., *Science* 265(5181):2096-2098 (1997)). In fiber-FISH, nucleic acid molecules are elongated and fixed on a surface by molecular combing. Hybridization with fluorescently labeled probe sequences allows determination of sequence landmarks on the nucleic acid molecules. The method requires fixation of elongated molecules so that molecular lengths and/or distances between markers can be measured. Pulse field gel electrophoresis can also be used to analyze the labeled nucleic acid molecules. Pulse field gel electrophoresis is described by Schwartz, D. C. et al., *Cell* 37(1):67-75 (1984). Other nucleic acid analysis systems are described by Otobe, K. et al., *Nucleic Acids Res.* 29(22):E109 (2001), Bensimon, A. et al. in U.S. Pat. No. 6,248,537, issued Jun. 19, 2001, Herrick, J. et al., *Chromosome Res.* 7(6):409:423 (1999), Schwartz in U.S. Pat. No. 6,150,089 issued Nov. 21, 2000 and U.S. Pat. No. 6,294,136, issued Sep. 25, 2001. Other linear polymer analysis systems can also be used, and the invention is not intended to be limited to solely those listed herein.

Optical detectable signals are generated, detected and stored in a database. The signals can be analyzed to determine structural information about the nucleic acid. The signals can be analyzed by assessing the intensity of the signal to determine structural information about the nucleic acid. The computer may be the same computer used to collect data about the nucleic acids, or may be a separate computer dedicated to data analysis. A suitable computer system to implement embodiments of the present invention typically includes an output device which displays information to a user, a main unit connected to the output device and an input device which receives input from a user. The main unit generally includes a processor connected to a memory system via an interconnection mechanism. The input device and output device also are connected to the processor and memory system via the interconnection mechanism. Computer programs for data analysis of the detected signals are readily available from CCD (charge coupled device) manufacturers.

The present invention is further illustrated by the following Examples, which in no way should be construed as further limiting. The entire contents of all of the references (including literature references, issued patents, published patent applications, and co-pending patent applications) cited throughout this application are expressly incorporated by reference herein.

EXAMPLES

Digital DNA™ Generally

Digital DNA™ is constructed using modular units. These modular units are represented by two Digital DNA™ blocks each approximately 10 kb in length. Exemplary blocks are illustrated in FIGS. 1 and 2. Each block consists of a structural fragment of 4.3 kb from *Autographa californica* followed by ~330 bp of Digital DNA™ identifier functional sequence which contains, as illustrated, no bis-PNA H binding sites (Block 0), or 3 or 6 bis-PNA H binding sites (Block 1). Each block further comprises additional structural sequence represented by a nonhomologous 4.8 kb fragment of *Autographa californica*, which follows the Digital DNA™ identifier functional sequence. The final segment of the block encodes the Digital DNA™ capture functional sequence. This sequence is uniform amongst blocks 0 and 1, and contains as illustrated 3 or 6 bis-PNA K binding sites. The 5' Zeocin resistance gene will not remain with the assembled Digital DNA™ but may be used in assembly as described herein.

Digital DNA™ Segment Synthesis

A modified common high-copy cloning plasmid, pBluescript, was used to construct the Digital DNA™ segments. pBluescript is a high-copy pUC based plasmid that is often used for cloning purposes. Numerous large pUC based plasmids exist with reports of some as large as 17 kb. In some embodiments, the final Digital DNA™ single segment vectors are approximately 13.5 kb (~3 kb vector and 10.5 kb insert).

Repetitive segments were cloned in an ordered fashion by the method described by Boe and Masson (1996 *NAR* 24: 2450-2451), as shown in FIG. 3. This method utilizes the directional ligation of compatible restriction endonuclease cohesive ends, A and B, with loss of both initial sites and creation of another upon ligation (e.g., X). This allows the continued "recycling" of the same restriction sites A and B as the construct size increases. The inclusion of the Zeocin resistance gene in the C-B region serves as a second selectable marker to aid in the isolation of the proper transformants. A similar method for production of many long direct repeats has also been described (Harrington et al. (1997) *Nature Genetics* 15: 345-355), and this method could also be employed to synthesize Digital DNA™.

pBluescript plasmid was modified by site specific mutagenesis to remove restriction endonuclease recognition sites from the polylinker in order to facilitate later cloning steps including the introduction of the Zeocin resistance gene into the remainder of the polylinker. The Zeocin resistance gene was amplified by PCR to contain a new polylinker sequence that contained all the necessary restriction sites that would be required for modular construction. An insertion of 650 bp was observed, as expected, following restriction digest (data not shown). In order to confirm that all polylinker sites were present, restriction endonuclease digestion of each enzyme was performed and each linearized the vector as was expected (data not shown).

Figure 4:
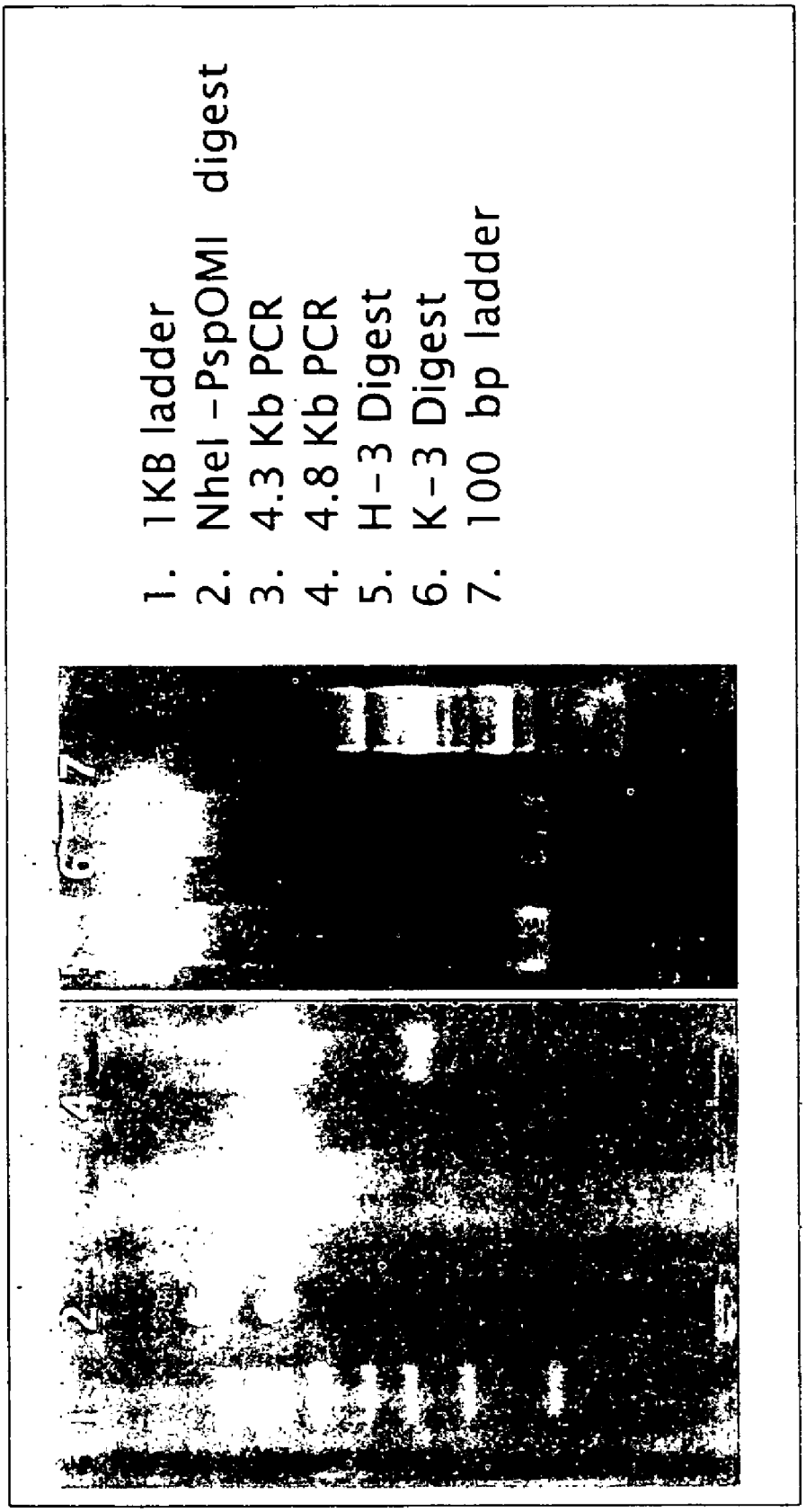
FIG. 4 is a photograph of an ethidium-stained gel showing the proper cloning of spacer, identifier and capture sequences into a plasmid vector.
Figure 5:
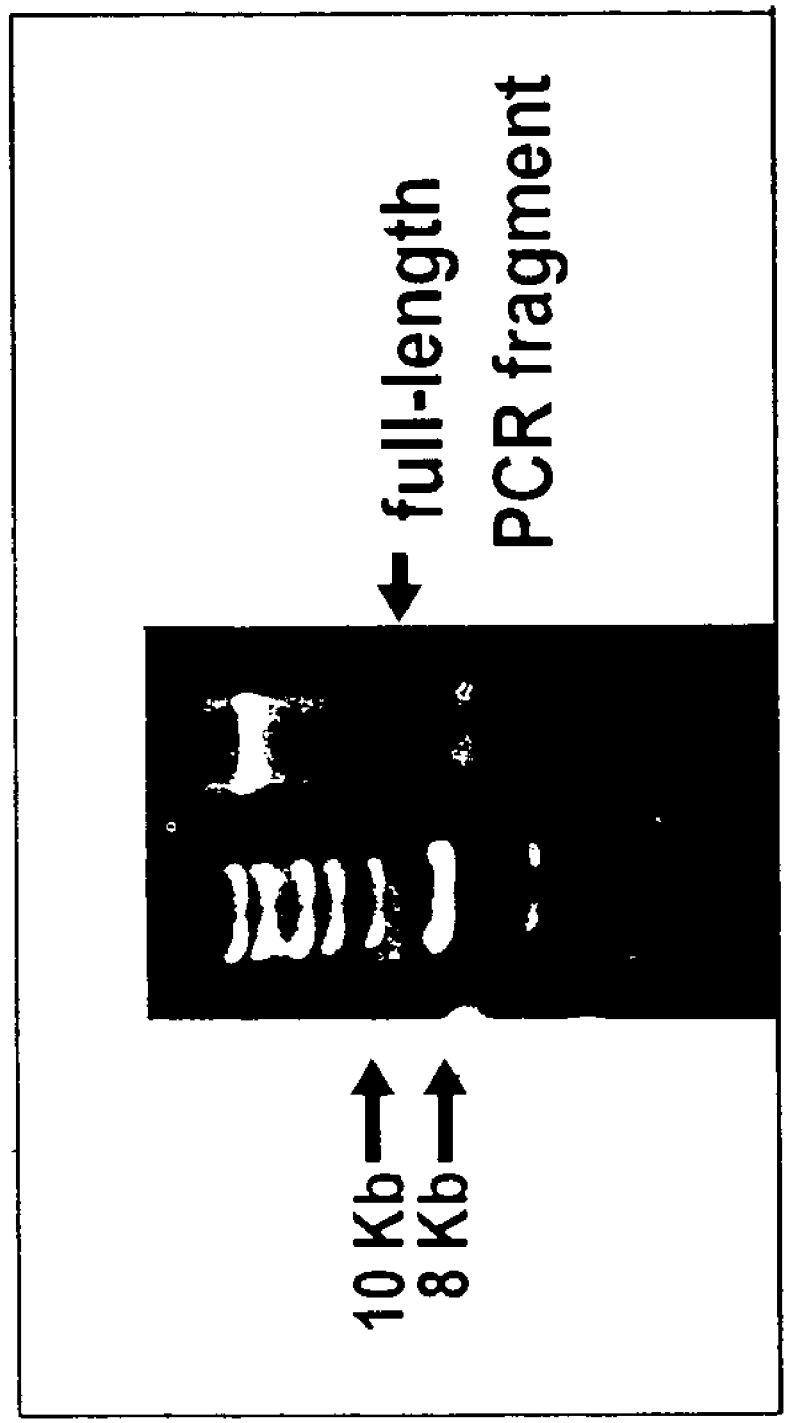
FIG. 5 is a photograph of an ethidium-stained gel showing the full length Digital DNA™ segment.

The first Digital DNA™ sequence to be inserted was the 4.8 kb structural fragments (i.e., spacer sequences) amplified by PCR from *Autographa californica*. Restriction endonuclease digestion confirmed the proper integration of the sequence (data not shown). Analyte capture functional sequence K-3 was next cloned and confirmed by restriction analysis. The cloning of the identifier sequence H-3 was next completed and the proper plasmid arrangement was confirmed. The final sequence to be added to the H-3/K-3 Digital DNA™ block was the 4.3 Kb NheI-PspOMI structural fragment (i.e., additional spacer sequence). This sequence has been cloned, and the presence of all DNA sequences has been confirmed by restriction digestion and PCR as shown in FIG. 4. Using the 5' PCR primer for the 4.3 kb fragment and the 3' PCR primer for the K-3 fragment, a PCR fragment of full length block H-3/K-3 was produced, as expected, from the proper block assembly, as shown in FIG. 5. In some embodiments, concatamers of the Digital DNA™ blocks may be ligated and amplified with PCR in order to limit the number of cloning steps required for extending Digital DNA™.

Digital DNA™ blocks can also be modified at their ends using nicking enzymes. Nicking enzymes recognize specific DNA sequences and create a site specific single strand nick. These enzymes are commercially available from commercial suppliers such as New England Biolabs. Nicking enzyme sites can be incorporated into oligonucleotide PCR primers used to amplify the Digital DNA™ blocks. When incubated with nicking enzyme, nicks near the ends of the DNA will cause the nicked strand to peel off as DNA "breaths", revealing sticky ends of a specific length and sequence. Temperature and salt concentrations can be varied to ensure that the small nicked strands are removed from the large duplex. Most of the sequence end proximal to the nick site can be altered such that each sticky end can be made unique. When Digital DNA™ blocks with different 5' sequences upstream of the nick sites are digested and ligated together, only blocks with compatible cohesive ends will ligate.

Many different sequences can be designed as cohesive ligation junctions and used for ordered assembly of Digital DNA™. The ability to generate a sticky end of any desired sequence also allows one to design sticky ends based on desired melting temperatures. The nicking enzyme generated sticky ends can be of any length. In one embodiment, they are 12 bases in length and have a melting temperature of ~36° C. This will allow the ligation of large molecules at higher temperatures than can be achieved with traditional restriction enzyme cohesive end ligations.

Digital DNA™ Segment Assembly

Digital DNA™ segments are transferred into the pCC1BAC plasmid. This is a single copy plasmid that is capable of maintaining very large DNA sequences of >200 kb. When introduced into *E. coli* strain, EPI300, (Epicenter Biotechnologies) and induced, the vector is capable of replicating to ~20 copies per cell while stably maintaining its size. The vector was modified to mutate restriction sites NotI at 3 bp and XbaI at 3182 bp. This facilitated cloning of particular Digital DNA™ segments.

Digital DNA™ can also be synthesized and/or extended using the pJAZZ-KA vector (Lucigen, Inc., Wisconsin). This is a linear vector that is propagated in *E. coli* with a maximum cloning size of 50 kb (e.g., the same size as 5 Digital DNA™ blocks as described above). These 50 kb pieces can then be cloned into pCC1BAC and added to as described by above.

The Cre/LoxP homologous recombination system can also be used to dimerize and tetramerize the 50 kb fragments in vitro using recombinant Cre protein and combinations of mutant LoxP sites that favor integration recombination. For this there could be three sets of different recognition sequences, two of which would allow the 50 kb pieces to dimerize, and the third which would allow the resulting 100 kb pieces to dimerize into 200 kb sequences. A two sequence set system could also be used. These sequences would then be cloned into the pCC1Bac vector by either normal restriction endonuclease cloning or the nick cloning described above. Cre/LoxP mutant recombination has been described by J. Thomson et al. Genesis 36: 162-167 (2003) and H. Albert et al. Plant Journal 7(4): 649-659 (1995).

Identifier and Capture Compounds

Various ways exist for attaching identifier and capture compounds units to the Digital DNA™. In the embodiments illustrated above, identifier and analyte capture sequences are recognized and bound by bis-PNAs. An alternate approach to binding functional sequences is through the use of triplex forming oligonucleotides (TFO) that bind in the major groove of the DNA without significant distortion of the DNA helix.

In one embodiment a polypyrimidine TFO binds to a site having an identical sequence (5'→3' polypurine duplex strand bound 5'→3' by a polypyrimidien TFO by Hoogsteen base pairing). In another embodiment, a polypurine TFO binds complementary (i.e., antiparallel) to a polypurine duplex strand by reverse Hoogsteen base pairing.

Two TFO binding sites have been identified in the BAC12M9 sequence (SEQ ID NO: 1: 5' AAA AAA AAA AAA AAA AAA AAA AAA AA 3' and SEQ ID NO:2: 5' AAA AAG AAA AAA GAA AAG 3'). 400 bp regions encompassing each site separately were amplified by PCR. Two TFO (15-mer and 18-mer) have been synthesized to bind to each target. LNA have been incorporated at every third base since their presence in TFO has been found to greatly increase triplex melting temperatures. In addition, the TFO are labeled with Alexa 546 dye at their 3' ends to aid in their detection.

TFO, bis-PNA and other identifier and analyte capture compounds can also be covalently attached to the Digital DNA™. Covalent attachment of such compounds will increase the stability and thus shelf-life of the Digital DNA™. Methods of photocrosslinking of the TFO to the duplex DNA involve 5' end labeling of TFO with psoralen, benzophenone, or acylazide or internal incorporation of bromodeoxyuridine.

EQUIVALENTS

It should be understood that the preceding is merely a detailed description of certain embodiments. It therefore should be apparent to those of ordinary skill in the art that various modifications and equivalents can be made without departing from the spirit and scope of the invention, and with no more than routine experimentation.

All references, patents and patent applications that are recited in this application are incorporated by reference herein in their entirety.

---

What is claimed is:

1. An isolated, non-naturally occurring nucleic acid comprising
    a non-specific spacer sequence,
    an identifier sequence, and
    an analyte capture sequence bound to an analyte adaptor compound that is covalently bound to an antibody or an antigen-binding antibody fragment,
    wherein the non-specific spacer sequence, the identifier sequence, and the analyte capture sequence are different nucleotide sequences, and wherein the nucleic acid is 7.5-15 kb in length.

2. The isolated, non-naturally occurring nucleic acid of claim 1, wherein the identifier sequence is located within the non-specific spacer sequence.

3. The isolated, non-naturally occurring nucleic acid of claim 1, wherein the identifier sequence comprises binding sites for identifier compounds.

4. The isolated, non-naturally occurring nucleic acid of claim 1, further comprising an identifier oligonucleotide bound to the identifier sequence.

5. The isolated, non-naturally occurring nucleic acid of claim 4, wherein the identifier oligonucleotide is a bis-peptide nucleic acid that is detectably labeled.

6. The isolated, non-naturally occurring nucleic acid of claim 4, wherein the identifier oligonucleotide is a triplex forming oligonucleotide that is detectably labeled.

7. The isolated, non-naturally occurring nucleic acid of claim 1, wherein the analyte adaptor compound is a PNA or triplex forming oligonucleotide.

8. An isolated, non-naturally occurring nucleic acid comprising
- a first plurality of identical, isolated, non-naturally occurring nucleic acids, each comprising a non-specific spacer sequence, an identifier sequence having a binding site for an identifier oligonucleotide, and an analyte capture sequence bound to PNA or a triplex forming oligonucleotide, and
- a second plurality of identical, isolated, non-naturally occurring nucleic acids that do not bind the identifier oligonucleotide, each comprising a non-specific spacer sequence, an identifier sequence lacking binding sites for the identifier oligonucleotide, and an analyte capture sequence bound to a PNA or a triplex forming oligonucleotide,
- wherein the non-specific spacer sequences and analyte capture sequences are identical between the pluralities, and members of the first and second plurality are 7.5-15 kb in length and are covalently linked to each other to form a pattern of identifier sequences.

9. A method of detecting an analyte comprising
- exposing a sample to the isolated, non-naturally occurring nucleic acid of claim 8 bound to analyte-specific binding partners, for a time and under conditions sufficient to allow an analyte, if present in the sample, to bind to the analyte-specific binding partners,
- exposing the sample to a secondary analyte-binding partner that comprises a detectable label,
- hybridizing identifier oligonucleotides comprising detectable labels, distinct from the detectable labels of the secondary analyte binding partner, to the nucleic acid, and
- determining (a) a pattern of detectably labeled identifier oligonucleotides hybridized to the nucleic acid and (b) an amount of secondary analyte-binding partner bound to the nucleic acid,
- wherein the pattern of detectably labeled identifier oligonucleotides hybridized to the nucleic acid identifies the analyte, and
- the amount of secondary analyte-binding partner bound to the nucleic acid that exceeds a control indicates the presence of analyte in the sample.

10. The method of claim 9, wherein the secondary analyte specific binding partner is an antibody or antigen-binding antibody fragment.

11. The isolated, non-naturally occurring nucleic acid of claim 8, further comprising an analyte specific binding partner bound to the PNA or triplex forming oligonucleotide.

12. The isolated, non-naturally occurring nucleic acid of claim 11, wherein the analyte specific binding partner is an antibody or an antigen-binding antibody fragment.

13. The isolated, non-naturally occurring nucleic acid of claim 11, wherein the analyte specific binding partner is a nucleic acid.

14. The isolated non-naturally occurring nucleic acid of claim 11, further comprising an identifier oligonucleotide hybridized to identifier sequence.

15. A method of synthesizing an isolated, non-naturally occurring nucleic acid comprising
- covalently assembling members of a first plurality of identical, isolated nucleic acids each comprising a non-specific spacer sequence, an identifier sequence having a binding site for an identifier oligonucleotide, and an analyte capture sequence with members of a second plurality of identical, isolated nucleic acids that do not bind the identifier oligonucleotide, each comprising a non-specific spacer sequence, an identifier sequence lacking binding sites for the identifier oligonucleotide, and an analyte capture sequence,
- wherein the non-specific spacer sequences and analyte capture sequences are identical between the pluralities, and members of the first and second plurality are 7.5-15 kb in length.

16. The method of claim 15, further comprising binding a PNA or triplex forming oligonucleotide to the analyte capture sequence.

17. The method of claim 16, further comprising covalently binding an antibody or antigen-binding antibody fragment to the PNA or triplex forming oligonucleotide.

18. The method of claim 16, further comprising covalently binding an aptamer to the PNA or triplex forming oligonucleotide.

19. An isolated, non-naturally occurring nucleic acid comprising
- a non-specific spacer sequence,
- an identifier sequence, and
- an analyte capture sequence bound to an analyte adaptor compound that is covalently bound to an aptamer,
- wherein the non-specific spacer sequence, the identifier sequence, and the analyte capture sequence are different nucleotide sequences, and wherein the nucleic acid is 7.5-15 kb in length.

20. The isolated, non-naturally occurring nucleic acid of claim 19, wherein the analyte adaptor compound is a PNA or triplex forming oligonucleotide.

* * * * *

UNITED STATES PATENT AND TRADEMARK OFFICE
CERTIFICATE OF CORRECTION

| | |
|---|---|
| PATENT NO. | : 7,595,160 B2 |
| APPLICATION NO. | : 11/364856 |
| DATED | : September 29, 2009 |
| INVENTOR(S) | : Eric Jon White et al. |

It is certified that error appears in the above-identified patent and that said Letters Patent is hereby corrected as shown below:

At column 33, line 7, please delete "bound to PNA" and replace with --bound to a PNA--.

Signed and Sealed this

Seventeenth Day of November, 2009

David J. Kappos
*Director of the United States Patent and Trademark Office*

SEQUENCE LISTING

```
<160> NUMBER OF SEQ ID NOS: 5

<210> SEQ ID NO 1
<211> LENGTH: 26
<212> TYPE: DNA
<213> ORGANISM: Artificial sequence
<220> FEATURE:
<223> OTHER INFORMATION: Synthetic sequence

<400> SEQUENCE: 1
aaaaaaaaaa aaaaaaaaa aaaaaa                                          26

<210> SEQ ID NO 2
<211> LENGTH: 18
<212> TYPE: DNA
<213> ORGANISM: Artificial sequence
<220> FEATURE:
<223> OTHER INFORMATION: Synthetic sequence

<400> SEQUENCE: 2 aaaagaaaa aagaaaag                                                    18

<210> SEQ ID NO 3
<211> LENGTH: 28
<212> TYPE: DNA
<213> ORGANISM: Artificial sequence
```

-continued

```
<220> FEATURE:
<223> OTHER INFORMATION: Synthetic sequence
<220> FEATURE:
<221> NAME/KEY: misc_feature
<222> LOCATION: (13)..(19)
<223> OTHER INFORMATION: N = any nucleotide and wherein any 1, 2, 3 or
      4 N's may be missing
<220> FEATURE:
<221> NAME/KEY: misc_feature
<222> LOCATION: (26)..(28)
<223> OTHER INFORMATION: n is a, c, g, or t

<400> SEQUENCE: 3
gtgtgttgcg cannnnnnnc ctagcnnn                                              28

<210> SEQ ID NO 4
<211> LENGTH: 31
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (12)..(18)
<223> OTHER INFORMATION: N = any nucleotide and wherein any 1, 2, 3 or
      4 N's may be missing

<400> SEQUENCE: 4
nnncctcagc annnnnnncc catggactca c                                          31

<210> SEQ ID NO 5
<211> LENGTH: 27
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (12)..(18)
<223> OTHER INFORMATION: N = any nucleotide and wherein any 1, 2, 3 or
      4 N's may be missing
<220> FEATURE:
<221> NAME/KEY: misc_feature
<222> LOCATION: (25)..(27)
<223> OTHER INFORMATION: n is a, c, g, or t

<400> SEQUENCE: 5
nnncctcagc annnnnnncc tagcnnn                                               27
```